US012330123B2

United States Patent
Makino et al.

(10) Patent No.: US 12,330,123 B2
(45) Date of Patent: Jun. 17, 2025

(54) IONIC LIQUID COMPOSITION FOR CARBON DIOXIDE SEPARATION MEMBRANE, CARBON DIOXIDE SEPARATION MEMBRANE HOLDING SAID COMPOSITION, AND CARBON DIOXIDE CONCENTRATION APPARATUS PROVIDED WITH SAID CARBON DIOXIDE SEPARATION MEMBRANE

(71) Applicants: NATIONAL INSTITUTE OF ADVANCED INDUSTRIAL SCIENCE AND TECHNOLOGY, Tokyo (JP); DAICEL CORPORATION, Osaka (JP)

(72) Inventors: Takashi Makino, Sendai (JP); Mitsuhiro Kanakubo, Sendai (JP); Masao Iwaya, Tokyo (JP); Yo Yamato, Tokyo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 484 days.

(21) Appl. No.: 17/798,745

(22) PCT Filed: Feb. 16, 2021

(86) PCT No.: PCT/JP2021/005629
§ 371 (c)(1),
(2) Date: Aug. 10, 2022

(87) PCT Pub. No.: WO2021/172087
PCT Pub. Date: Sep. 2, 2021

(65) Prior Publication Data
US 2023/0099980 A1 Mar. 30, 2023

(30) Foreign Application Priority Data

Feb. 25, 2020 (JP) ................ 2020-029112

(51) Int. Cl.
*B01D 69/14* (2006.01)
*B01D 53/22* (2006.01)
(Continued)

(52) U.S. Cl.
CPC ........ *B01D 69/1411* (2022.08); *B01D 53/228* (2013.01); *B01D 69/1213* (2022.08);
(Continued)

(58) Field of Classification Search
CPC . B01D 69/1213; B01D 69/1411; C07C 53/10; C07C 59/125; C07C 211/63
See application file for complete search history.

(56) References Cited

U.S. PATENT DOCUMENTS

2013/0195744 A1 8/2013 Janiczek et al.
2014/0283839 A1 9/2014 Wickham et al.

FOREIGN PATENT DOCUMENTS

JP 2006-036950 A 2/2006
JP 2006-305544 A 11/2006
(Continued)

OTHER PUBLICATIONS

EP Extended Search Report dated Feb. 13, 2024 for EP Patent Application No. 21760455.2.
(Continued)

*Primary Examiner* — Robert Clemente
(74) *Attorney, Agent, or Firm* — HAUPTMAN HAM, LLP

(57) ABSTRACT

Provide are an ionic liquid composition for a carbon dioxide separation membrane, a carbon dioxide separation membrane retaining the composition in voids, and a carbon
(Continued)

dioxide concentration apparatus provided with the carbon dioxide separation membrane that can be used to separate carbon dioxide from high partial pressure to low partial pressure. The permeability of $CO_2$ and $CO_2$ selectivity ratio of the carbon dioxide separation membrane can be improved, and carbon dioxide from high partial pressure to a low partial pressure of 1 kPa or lower can be selectively separated and recycled by using an ionic liquid composition prepared by combining: an ionic liquid (I) that is an aminium having one or more primary or secondary amino groups and an ethylenediamine or propylenediamine backbone in the cation; and an ionic liquid (II) in which the cation has no primary or secondary amino group and the anion is an oxoacid anion.

14 Claims, 27 Drawing Sheets

(51) Int. Cl.
| | | |
|---|---|---|
| *B01D 69/12* | (2006.01) | |
| *B01D 71/02* | (2006.01) | |
| *B01D 71/36* | (2006.01) | |
| *C07C 53/10* | (2006.01) | |
| *C07C 59/125* | (2006.01) | |
| *C07C 211/63* | (2006.01) | |
| *C07C 311/48* | (2006.01) | |
| *C07D 233/58* | (2006.01) | |

(52) U.S. Cl.
CPC ............. *B01D 71/05* (2022.08); *B01D 71/36* (2013.01); *C07C 53/10* (2013.01); *C07C 59/125* (2013.01); *C07C 211/63* (2013.01); *C07C 311/48* (2013.01); *C07D 233/58* (2013.01)

(56) References Cited

FOREIGN PATENT DOCUMENTS

| | | |
|---|---|---|
| JP | 2009-106909 A | 5/2009 |
| JP | 2010-214324 A | 9/2010 |
| JP | 2011-510811 A | 4/2011 |
| JP | 2012-055785 A | 3/2012 |
| JP | 2016-010760 A | 1/2016 |
| JP | 2016-077935 A | 5/2016 |
| JP | 2017-104775 A | 6/2017 |
| WO | 2013/118776 A1 | 8/2013 |
| WO | 2018/012459 A1 | 1/2018 |
| WO | 2018/211945 A1 | 11/2018 |

OTHER PUBLICATIONS

Vijayraghavan R et al., "Diamino protic ionic liquids for CO2 capture", Physical Chemistry Chemical Physics, vol. 15, No. 46, Jan. 1, 2013, p. 19994.

Vijayaraghavan R et al., "Base-rich diamino protic ionic liquid mixtures for enhanced CO2 capture", Separation and Purification Technology, vol. 196, May 1, 2018, pp. 27-31.

Shaojuan Zeng et al., "Ionic-Liquid-Based CO 2 Capture Systems: Structure, Interaction and Process" Chemical Reviews, vol. 117, No. 14, Jul. 26, 2017, pp. 9625-9673.

Mitsuhisa Kanakubo et al., "Solvent Effects on CO2 Absorbency of Amine Compounds in Non-Aqueous Solvents", 40th Symposium on Solution Chemistry of Japan, Oct. 18, 2017.

Takashi Makino, et., al., "Effect of Inclusion of 1-Butyl-3-Methylimidazolium Trifluoromethanesulfonate on CO2 and N2Permeabilities for PVDF and PVDF-HFP Membranes" International Journal of Membrane Science and Technology, 2015, 2, 14-20.

Kenta Fuji, et al., "Carbon Dioxide Separation Using a High-toughness Ion Gel with a Tetra-armed Polymer Network" Chemistry Letters, 2015, 44, 17-19.

PCT/ISA/210, "International Search Report for PCT International Application No. PCT/JP2021/005629," Apr. 20, 2021.

IONIC LIQUID COMPOSITION FOR CARBON DIOXIDE SEPARATION MEMBRANE, CARBON DIOXIDE SEPARATION MEMBRANE HOLDING SAID COMPOSITION, AND CARBON DIOXIDE CONCENTRATION APPARATUS PROVIDED WITH SAID CARBON DIOXIDE SEPARATION MEMBRANE

RELATED APPLICATIONS

The present application is National Phase of International Application No. PCT/JP2021/005629 filed Feb. 16, 2021, and claims priority from Japanese Application No. 2020-029112, filed Feb. 25, 2020, the disclosure of which is hereby incorporated by reference herein in its entirety.

TECHNICAL FIELD

The present invention relates to an ionic liquid composition for a carbon dioxide separation membrane, a carbon dioxide separation membrane retaining the composition, and a carbon dioxide concentration apparatus provided with the carbon dioxide separation membrane.

BACKGROUND ART

A technology to separate and recover carbon dioxide is necessary for the production of hydrogen and methane from natural gas as a raw material, maintenance of living environments in closed conditions, such as in outer space and under the sea, and the like. In addition, from the viewpoint of reducing the amount of greenhouse gas emissions, the technology has been actively studied for large emission sources, such as thermal power plants and ironworks, and also for carbon dioxide fertilization in the agricultural sector.

Representative gas separation technologies known for carbon dioxide include:

(1) a chemical absorption method, in which carbon dioxide is separated by selectively absorbing carbon dioxide into a solvent from a mixed gas containing carbon dioxide by a chemical reaction, and then carbon dioxide is recovered by stripping carbon dioxide from the solvent by a reverse reaction;

(2) a physical absorption method for separating and recovering carbon dioxide, in which carbon dioxide is separated by absorbing carbon dioxide physically, not by chemical reaction, into a solvent selectively from a mixed gas containing carbon dioxide, and carbon dioxide is recovered by stripping carbon dioxide from the solvent by decompression; and (3) a membrane separation method, in which a gas containing carbon dioxide, the gas to be separated, is fed from one side of a membrane, and carbon dioxide in the gas is selectively transported to the other side of the membrane to separate using the partial pressure difference of carbon dioxide between the front and rear sides of the membrane.

Ionic liquids are typically liquid salts composed of only a cation and an anion and having a melting point at or near or below room temperature. Examples of the characteristics of ionic liquids include being liquid in a wide temperature range, having a very low vapor pressure (non-volatile), being flame retardant, having excellent heat resistance and chemical stability, having a wide potential window and high ionic conductivity, and being capable of dissolving a variety of chemical species.

Thus, ionic liquids have been extensively studied as electrolytes for electrochemical devices; solvents in various processes, such as separation and purification, and organic reactions; and functional materials, such as actuators and lubricants.

Ionic liquids have these properties, especially non-volatility and low specific heat, which are required for absorption liquids for carbon dioxide, and thus are investigated for use as absorption liquids for carbon dioxide also in the separation and recovery technology of carbon dioxide.

For example, chemical absorption methods using an ionic liquid as an absorption liquid or solvent have been proposed, including using a chemically absorbing ionic liquid, such as an ionic liquid having an amino group in the cation, as the absorption liquid (Patent Documents 1, 2, and 3) and using an ionic liquid as a solvent in a non-aqueous absorption liquid containing an amine compound (Patent Document 4 and Non-Patent Literature 1).

In addition, physical absorption methods using an ionic liquid with excellent physical absorption properties as an absorption liquid have been proposed, such as, for example, using an ionic liquid prepared using an imidazolium-based cation having no amino group in the cation (Patent Documents 5 to 8).

On the other hand, the membrane separation method separates gases using the difference in the solubility to the membrane and the difference in diffusivity in the membrane and thus is required to improve both the permeability and selectivity ratio of carbon dioxide to improve the separation efficiency of carbon dioxide. However, in polymer membranes used as carbon dioxide separation membranes in the related art, increasing the selectivity ratio is known to decrease the permeability, and this has limited the improvement of the permeability and selectivity ratio of carbon dioxide using a polymer membrane.

To overcome this limitation, using a substance called a carrier, which chemically reacts selectively and reversibly with a specific component in the gas to be separated and transports the specific component, is believed to be effective.

When a liquid membrane containing the carrier is used as a separation membrane for carbon dioxide, the selective transport based on the chemical reaction of carbon dioxide with the carrier is used. Thus, this enables carbon dioxide to be separated with a high selectivity ratio compared with using a polymer membrane known in the art, and the permeation rate of carbon dioxide in the membrane is often high. However, in a membrane prepared using a common solvent having volatility, the gas separation function of the membrane is deactivated by the volatilization loss of the solvent, and thus the membrane cannot be used over a long period of time.

Thus, using a liquid membrane containing a non-volatile ionic liquid as a carrier instead of a solvent having volatility has been proposed.

For example, a liquid membrane containing an ionic liquid having an amino group in the cation has been proposed, and Patent Document 1 above describes using a porous liquid membrane as a carbon dioxide separation membrane, the porous liquid membrane impregnated with an absorption liquid containing an ionic liquid as a main component, the ionic liquid having a primary amino group in the cation.

In addition, in Patent Document 9, an ionic liquid composed of a cation having an amino group, such as 1-(3-aminopropyl)-3-methylimidazolium, in a liquid membrane retaining the ionic liquid in voids in a porous membrane intended to separate and recover carbon dioxide is used.

Furthermore, carbon dioxide separation membranes prepared using an ionic liquid having an imidazolium-based cation, such as 1,3-dialkylimidazolium, have also been proposed (Patent Documents 10 and 11, and Non-Patent Literatures 2 and 3).

Moreover, Patent Document 12 proposes a separation membrane including an ionic liquid affinitive porous layer retaining an ionic liquid-containing liquid in voids as a carbon dioxide separation membrane suitable for carbon dioxide fertilization in the agricultural sector. The document describes examples of the ionic liquid for use in the separation membrane, the ionic liquid containing: a cation selected from ammoniums, imidazoliums, and phosphoniums; and an anion selected from fluorine-containing anions, cyano group-containing anions, and amino acid-derived anions. The document describes that among others, the ionic liquid is preferably an ionic liquid, such as $[P_{4444}][Pro]$, prepared by combining a phosphonium represented by a chemical formula $[R_3R'P]^+$, where R is an alkyl group having from 2 to 6 carbons and R' is an alkyl group having from 4 to 16 carbons, and an anion derived from proline.

CITATION LIST

Patent Document

Patent Document 1: JP 2006-036950 A
Patent Document 2: JP 2012-055785 A
Patent Document 3: JP 2016-10760 A
Patent Document 4: JP 2017-104775 A
Patent Document 5: JP 2006-305544 A
Patent Document 6: JP 2009-106909 A
Patent Document 7: JP 2011-510811 T
Patent Document 8: JP 2016-077935 A
Patent Document 9: US 2014/0,283,839 A
Patent Document 10: JP 2010-214324 A
Patent Document 11: WO 2013/118776
Patent Document 12: WO 2018/211945

Non-Patent Literature

Non-Patent Literature 1: Mitsuhisa Kanakubo et al. "Solvent Effects on CO2 Absorbency of Amine Compounds in Non-Aqueous Solvents", 40th Symposium on Solution Chemistry of Japan, Oct. 18, 2017
Non-Patent Literature 2: Takashi Makino, et., al. International Journal of Membrane Science and Technology, 2015, 2, 14-20
Non-Patent Literature 3: Kenta Fuji, et. al., Chemistry Letters, 2015, 44, 17-19

SUMMARY OF INVENTION

Technical Problem

A technology to separate and recover carbon dioxide with high efficiency is required to effectively use an unutilized carbon dioxide as a carbon source. Although a technology to separate and recover carbon dioxide at high concentration (high partial pressure) has been mainly developed in the related art, in recent years, on the assumption of separation and recovery from various carbon dioxide emission sources, a technology to separate and recover carbon dioxide at low concentration (low partial pressure), such as carbon dioxide in the atmosphere, also needs to be developed.

Thus, the membrane separation method using a carrier described above, the method having a potential to achieve high carbon dioxide permeation selectivity, is expected as one of the promising separation and recovery technologies.

For example, Patent Document 11 discloses that a carbon dioxide permeable membrane having an amino acid ionic liquid and a porous membrane impregnated with the amino acid ionic liquid, the amino acid ionic liquid containing from 3 to 50 mass % of water, maintains high carbon dioxide permeability and carbon dioxide/nitrogen selectivity even when the partial pressure of carbon dioxide is low, and also describes that the carbon dioxide partial pressure in the mixed gas may be 15 kPa. Furthermore, the document illustrates results of measurements performed by varying the partial pressure in the range from 2 to 30 kPa specifically using $[P_{4444}][Gly]$ or [emim][Gly] having a glycine-derived anion.

However, a carbon dioxide separation membrane that can efficiently separate carbon dioxide to a low partial pressure of 1 kPa or lower has not yet been found.

The present invention has been made in view of such a current status, and an object of the present invention is to provide an ionic liquid composition for a carbon dioxide separation membrane, a carbon dioxide separation membrane retaining the composition in voids, and a carbon dioxide concentration apparatus provided with the carbon dioxide separation membrane which can be used to separate carbon dioxide from high partial pressure to low partial pressure, especially 1 kPa or lower.

Solution to Problem

To efficiently separate and recover carbon dioxide in the atmosphere using a liquid membrane containing an ionic liquid, the selectivity ratio of carbon dioxide ($CO_2$) to Nitrogen ($N_2$) (hereinafter described as the "$CO_2$ selectivity ratio") as well as the permeability of carbon dioxide needs to be improved under low carbon dioxide partial pressure conditions.

In the membrane separation method, gas permeability is expressed as the product of solubility of the gas and diffusion rate of the gas. To improve the permeability of $CO_2$ and $CO_2$ selectivity ratio in a membrane liquid containing an ionic liquid as a carrier, the following are important: to increase the solubility of carbon dioxide in the ionic liquid as the carrier; also to reduce the solubility of nitrogen; and further to improve the diffusion rate of the carrier that has chemically reacted with carbon dioxide.

Thus, inventors attempted to use an ionic liquid prepared using an aminium having one or more primary or secondary amino groups and an ethylenediamine or propylenediamine backbone, the ionic liquid described in Patent Document 3 above as an ionic liquid having excellent chemical absorbency, and an ionic liquid described in the Patent Document 3, the ionic liquid used as a diluent, but found that these ionic liquids cannot improve the permeation selectivity of carbon dioxide (see Comparative Examples 1 to 8 described later).

Thus, as a result of further investigations, the inventors found that the permeability of $CO_2$ and $CO_2$ selectivity ratio of a carbon dioxide separation membrane can be improved by using an ionic liquid composition prepared by combining: an ionic liquid (I) that is an aminium having one or more primary or secondary amino groups and an ethylenediamine or propylenediamine backbone in the cation; and an ionic liquid (II) in which the cation has no primary or secondary amino group and the anion is an oxoacid anion. Furthermore, the inventors also found that using the ionic liquid composition can selectively separate and recycle even carbon dioxide at low partial pressure.

The present invention is completed based on the findings described above and employs the following means to solve the above object.

[1] An ionic liquid composition for a carbon dioxide separation membrane, the ionic liquid composition being used in a carbon dioxide separation membrane, the ionic liquid composition containing:
an ionic liquid (I); and
an ionic liquid (II), wherein
a cation in the ionic liquid (I) is an aminium having:
one or more primary or secondary amino groups; and
an ethylenediamine or propylenediamine backbone, and
in the ionic liquid (II),
a cation has no primary or secondary amino group, and
an anion is an oxoacid anion.

[2] The ionic liquid composition for a carbon dioxide separation membrane according to [1], wherein the aminium is one or more selected from 2-aminoethylaminium, 2-(N-hydroxyethylamino)ethylaminium, 3-aminopropylaminium, 3-(N-methylamino)propylaminium, 2-(2-(aminoethyl)amino)ethylaminium, and 2-(2-(2-(aminoethyl)aminoethyl)amino)ethylaminium.

[3] The ionic liquid composition for a carbon dioxide separation membrane according to [1] or [2], wherein the anion of the ionic liquid (I) is bis(trifluoromethylsulfonyl)amide.

[4] The ionic liquid composition for a carbon dioxide separation membrane according to any of [1] to [3], wherein the oxoacid anion is one or more selected from carboxylates, phosphates, and phosphonates.

[5] The ionic liquid composition for a carbon dioxide separation membrane according to [4], wherein the oxoacid anion is one or more selected from acetate, 2-(1-methoxyethoxy)propionate, and methylphosphonate.

[6] The ionic liquid composition for a carbon dioxide separation membrane according to [4] or [5], wherein the cation of the ionic liquid (II) is one or more selected from 1-ethyl-3-methylimidazolium, N,N-diethyl-N-methyl-N-heptylammonium, and N,N-diethyl-N-methyl-N-(6-hydroxyhexyl)ammonium.

[7] A carbon dioxide separation membrane retaining the ionic liquid composition for a carbon dioxide separation membrane described in any of [1] to [6].

[8] The carbon dioxide separation membrane according to [7], wherein the carbon dioxide separation membrane includes:
an ionic liquid affinitive porous layer retaining the ionic liquid composition for a carbon dioxide separation membrane in voids; and
an ionic liquid non-affinitive porous layer.

[9] The carbon dioxide separation membrane according to [8], wherein the ionic liquid affinitive porous layer includes an inorganic material.

[10] The carbon dioxide separation membrane according to [9], wherein the inorganic material contains metal oxide particles with an average particle size from 0.001 to 5 μm on a number basis.

[11] The carbon dioxide separation membrane according to any of [8] to [10], wherein an average thickness of the ionic liquid affinitive porous layer is from 0.01 to 10 μm.

[12] The carbon dioxide separation membrane according to any of [7] to [11], wherein the carbon dioxide separation membrane is used to separate and concentrate carbon dioxide having a partial pressure of 1 kPa or lower.

[13] A carbon dioxide concentration apparatus provided with the carbon dioxide separation membrane described in any of [7] to [12].

Advantageous Effects of Invention

The ionic liquid composition for a carbon dioxide separation membrane according to an embodiment of the present invention can improve permeability of $CO_2$ and $CO_2$ selectivity ratio, and can efficiently separate and recover carbon dioxide from high partial pressure to a low partial pressure of 1 kPa or lower.

Figure 17:
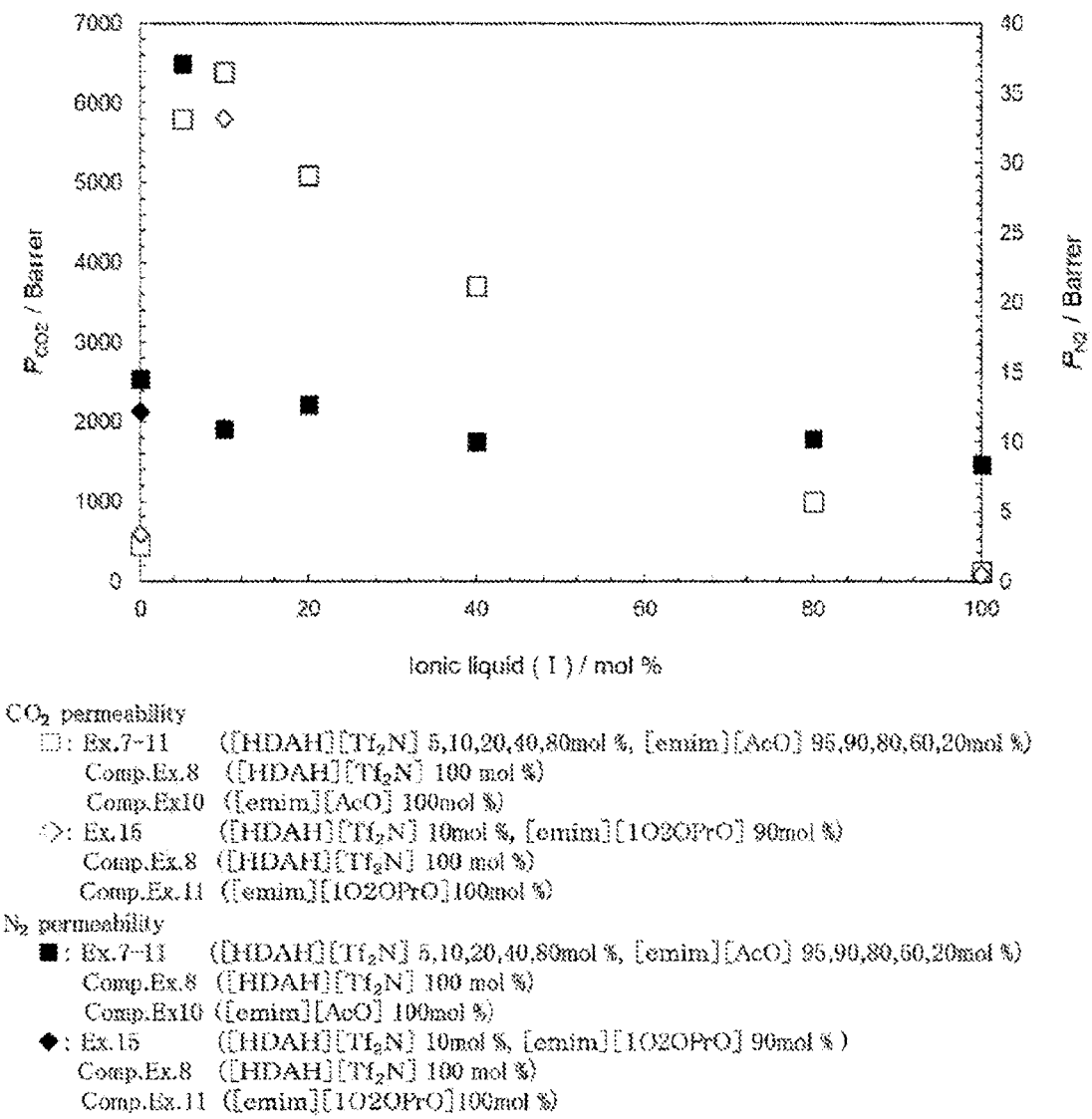

FIG. 17 is a graph showing composition dependences of $CO_2$ selectivity ratios and $N_2$ permeability coefficients of [emim][AcO]-based and [emim][1O2OPrO]-based $CO_2$ separation membranes (Examples 7 to 11, and 15, and Comparative Examples 8, 10, and 11).

Figure 18:
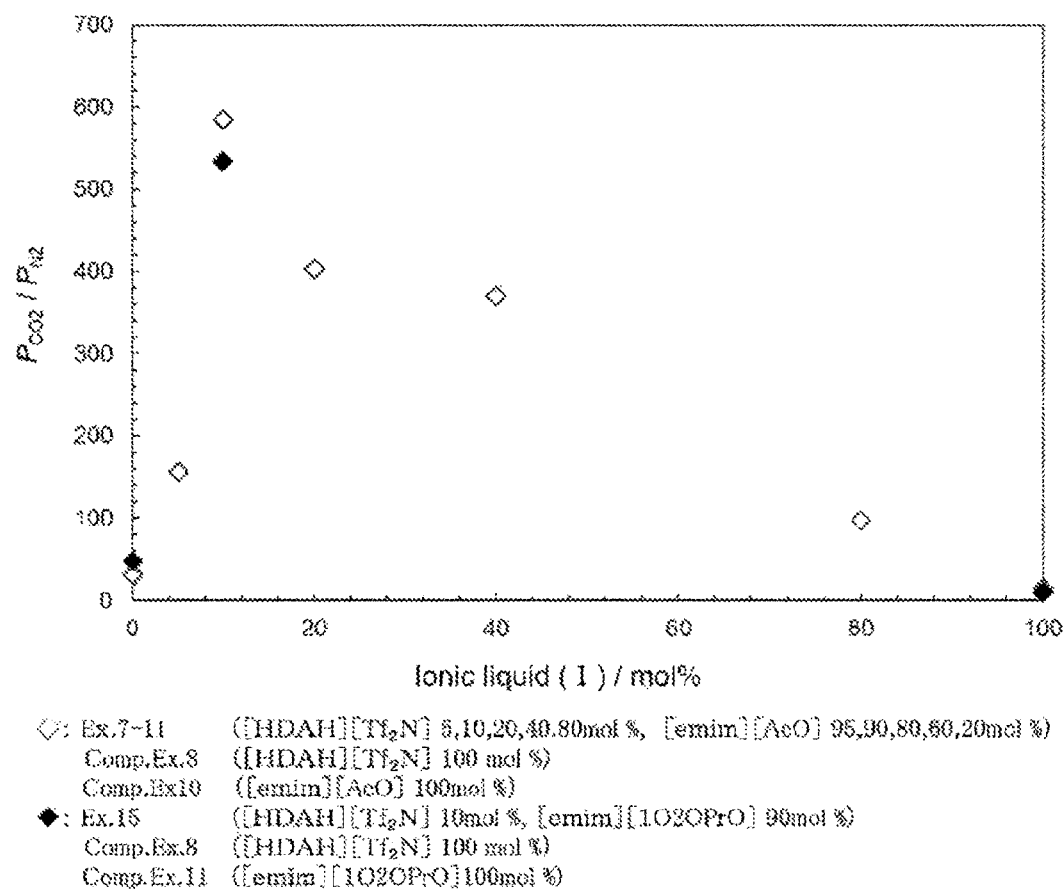

FIG. 18 is a graph showing composition dependences of $CO_2$ selectivity ratios of the [emim][AcO]-based and [emim][1O2OPrO]-based $CO_2$ separation membranes (Examples 7 to 11, and 15, and Comparative Examples 8, 10, and 11).

Figure 19:
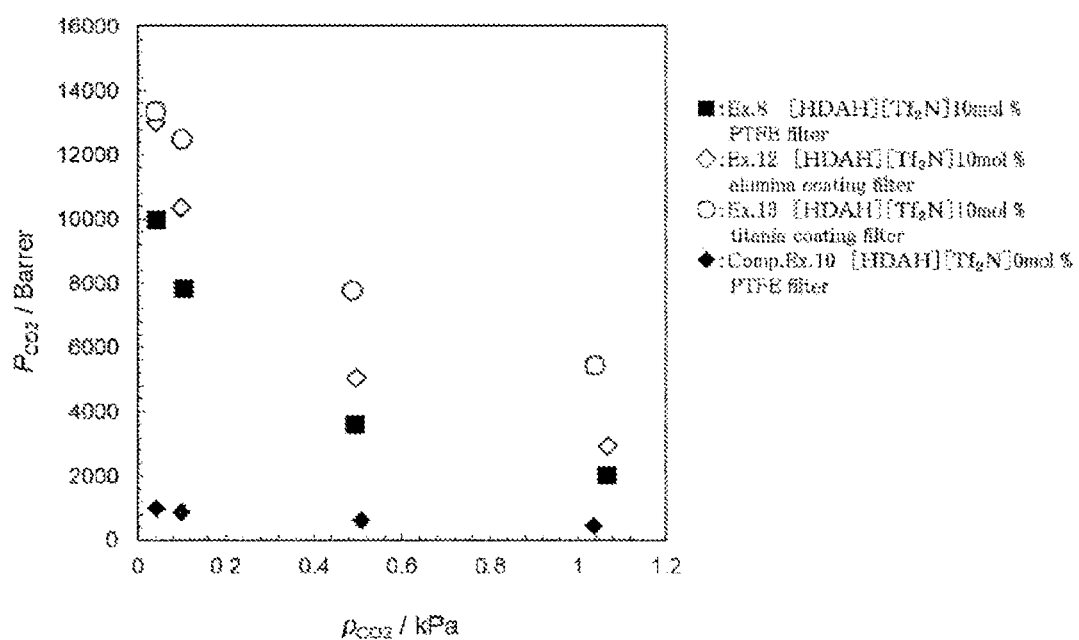

FIG. 19 is a graph showing $CO_2$ partial pressure dependences of $CO_2$ permeability coefficients of the [emim][AcO]-based $CO_2$ separation membranes (Examples 8, 12, and 13, and Comparative Example 10).

Figure 20:
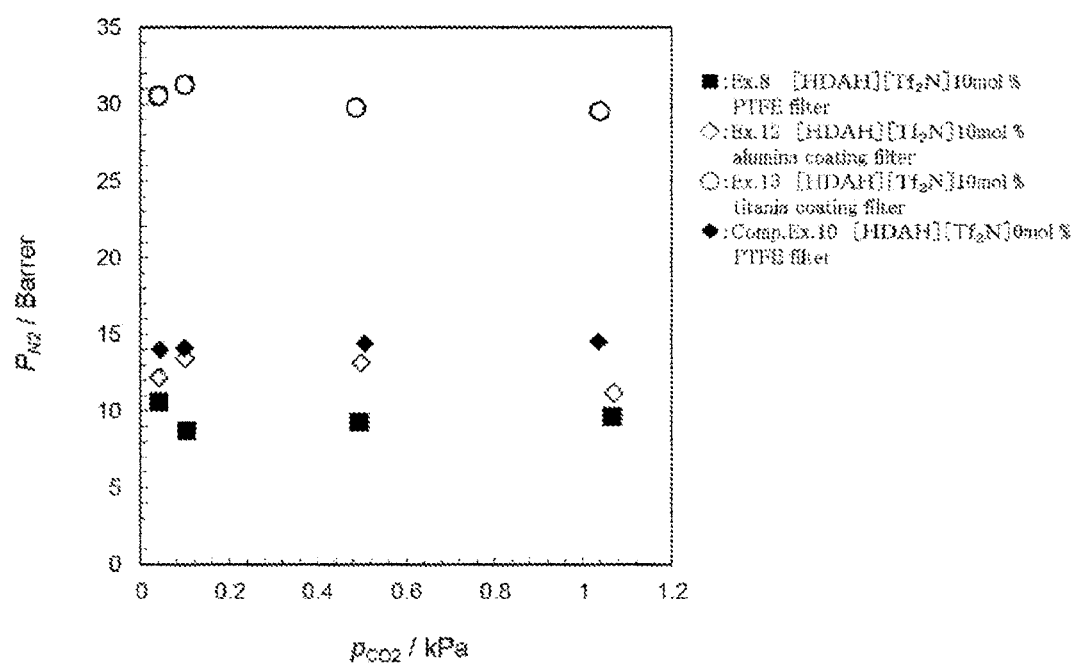

FIG. 20 is a graph showing $CO_2$ partial pressure dependences of $N_2$ permeability coefficients of the [emim][AcO]-based $CO_2$ separation membranes (Examples 8, 12, and 13, and Comparative Example 10).

Figure 21:
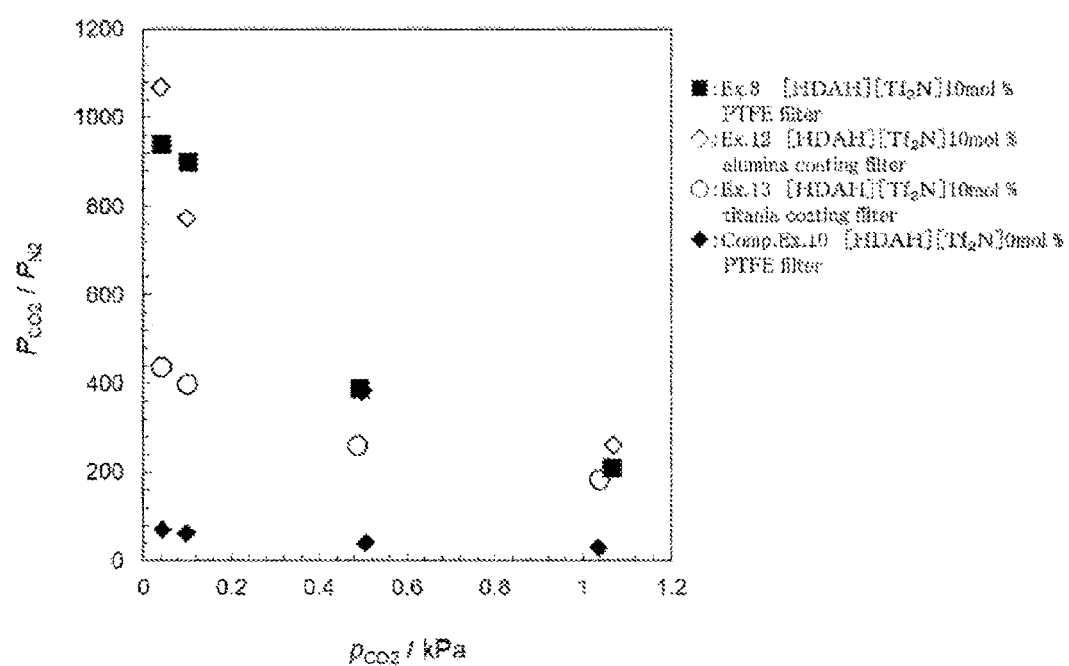

FIG. 21 is a graph showing $CO_2$ partial pressure dependences of $CO_2$ selectivity ratios of the [emim][AcO]-based $CO_2$ separation membranes (Examples 8, 12, and 13, and Comparative Example 10).

Figure 22:
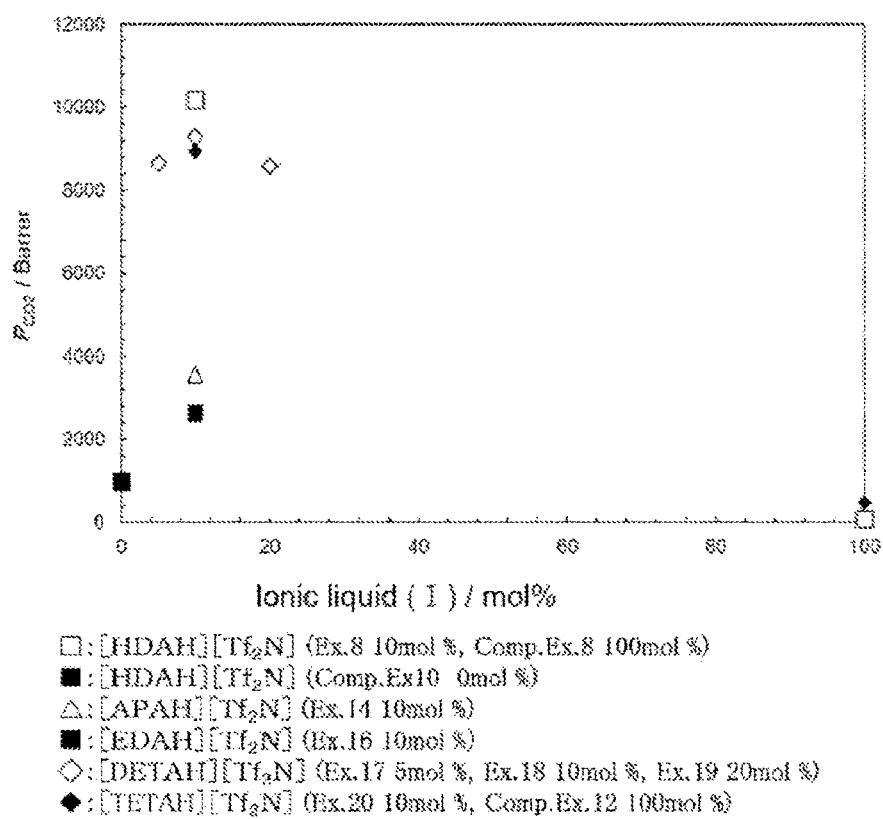

FIG. 22 is a graph showing composition dependences of $CO_2$ permeability coefficients of the [emim][AcO]-based (amine change) $CO_2$ separation membranes (Examples 8, 14, and 16 to 20, and Comparative Examples 8, 10, and 12).

Figure 23:
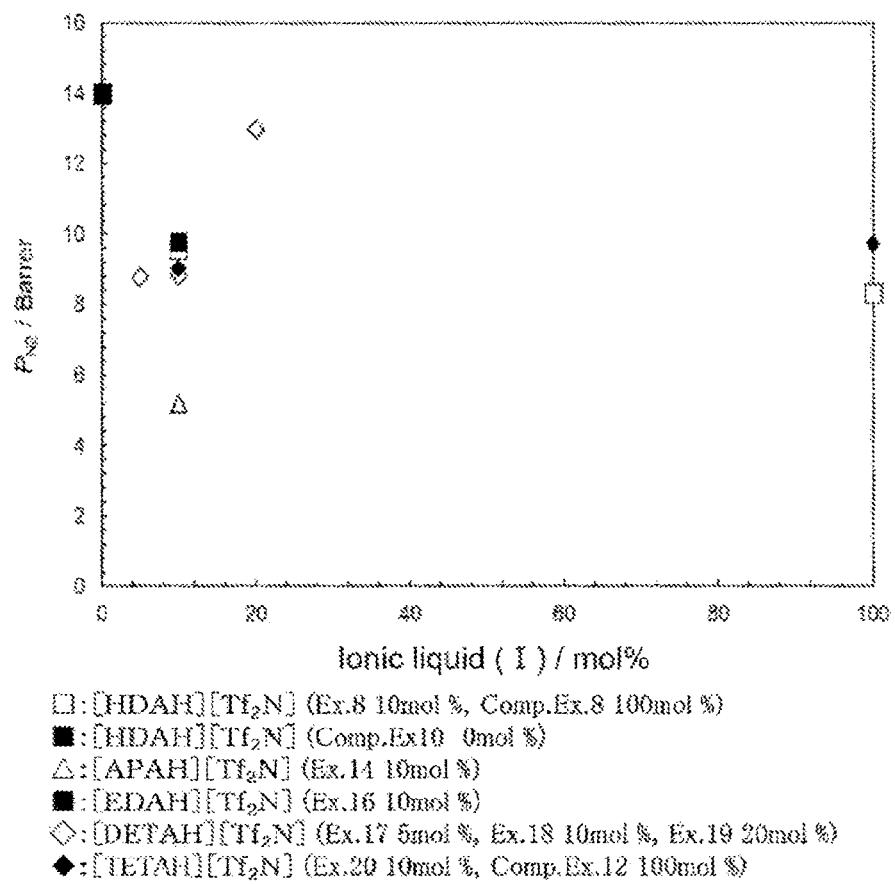

FIG. 23 is a graph showing composition dependences of $N_2$ permeability coefficients of the [emim][AcO]-based (amine change) $CO_2$ separation membranes (Examples 8, 14, and 16 to 20, and Comparative Examples 8, 10, and 12).

Figure 24:
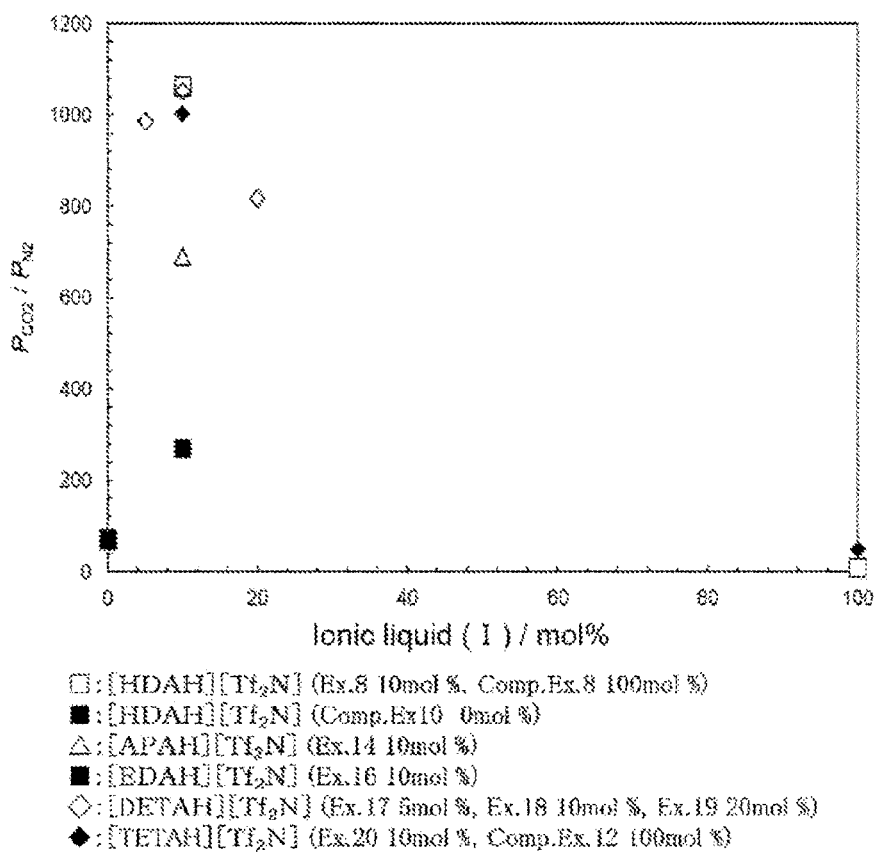

FIG. 24 is a graph showing composition dependences of $CO_2$ selectivity ratios of the [emim][AcO]-based (amine change) $CO_2$ separation membranes (Examples 8, 14, and 16 to 20, and Comparative Examples 8, 10, and 12).

Figure 25:
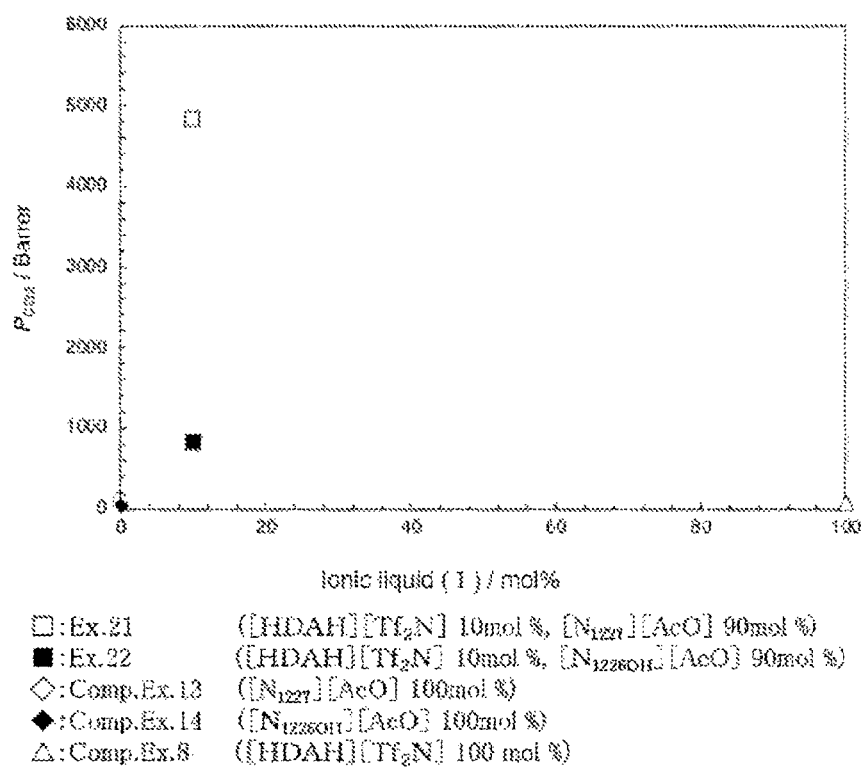

FIG. 25 is a graph showing composition dependences of $CO_2$ permeability coefficients of $[N_{1227}]$[AcO]-based and $[N_{1226OH}]$[AcO]-based $CO_2$ separation membranes (Examples 21 and 22, and Comparative Examples 8, 13, and 14).

Figure 26:
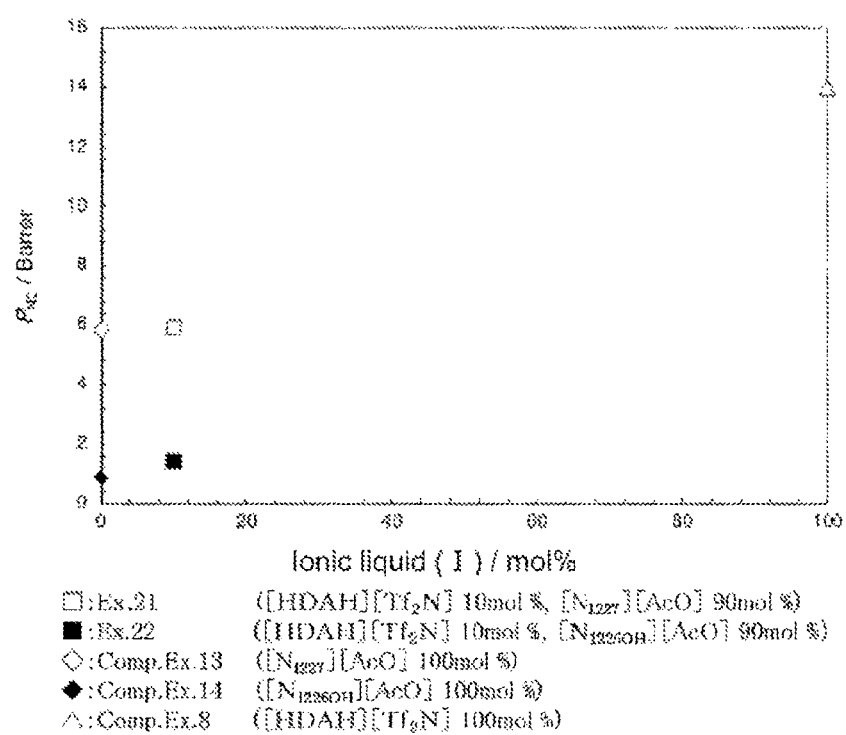

FIG. 26 is a graph showing composition dependences of $N_2$ permeability coefficients of the $[N_{1227}]$[AcO]-based and $[N_{1226OH}]$[AcO]-based $CO_2$ separation membranes (Examples 21 and 22, and Comparative Examples 8, 13, and 14).

Figure 27:
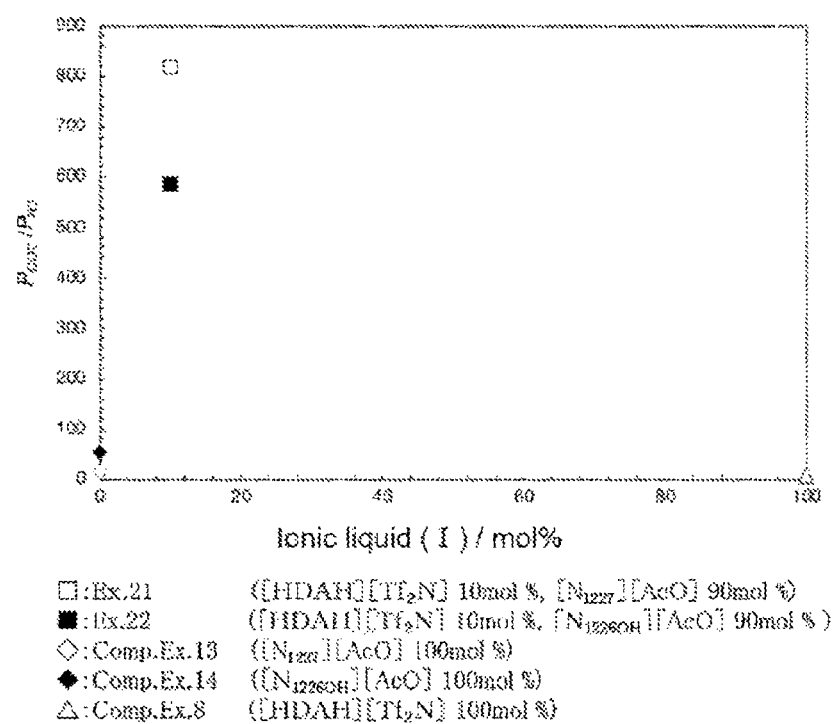

FIG. 27 is a graph showing composition dependences of $CO_2$ selectivity ratios of the $[N_{1227}]$[AcO]-based and $[N_{1226OH}]$[AcO]-based $CO_2$ separation membranes (Examples 21 and 22, and Comparative Examples 8, 13, and 14).

DESCRIPTION OF EMBODIMENTS

An embodiment of the present invention is an ionic liquid composition for a carbon dioxide separation membrane, the ionic liquid composition being used in a carbon dioxide separation membrane, the ionic liquid composition containing:
  an ionic liquid (I); and
  an ionic liquid (II), in which
  a cation in the ionic liquid (I) is an aminium having:
  one or more primary or secondary amino groups; and
  an ethylenediamine or propylenediamine backbone, and in the ionic liquid (II),
  a cation has no primary or secondary amino group, and an anion is an oxoacid anion.

Hereinafter, the ionic liquid composition for a carbon dioxide separation membrane, a carbon dioxide separation membrane retaining the composition, and a carbon dioxide concentration apparatus provided with the carbon dioxide separation membrane according to embodiments of the present invention will be described in detail sequentially, but these are intended to describe embodiments of the present invention and not to limit the scope of the invention.

In addition, "to" indicating a numerical range includes the numerical values described before and after "to" as the lower limit and the upper limit.

Ionic Liquid (I)

The ionic liquid (I) in the ionic liquid composition for a carbon dioxide separation membrane according to an embodiment of the present invention is an ionic liquid in which the cation is an aminium having one or more primary or secondary amino groups and an ethylenediamine or propylenediamine backbone.

Cation

The cation in the ionic liquid (I) according to an embodiment of the present invention is an aminium having a primary amino group in which one carbon atom and two hydrogens are bonded to one nitrogen atom or a secondary amino group in which two carbon atoms and one hydrogen are bonded to one nitrogen atom.

The aminium has at least one ethylenediamine backbone or propylenediamine backbone, and the aminium having one ethylenediamine backbone is represented by a general formula below.

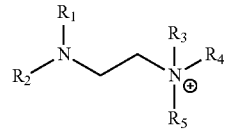

[Chem. 1]

where $R_1$ and $R_2$ both represent a hydrogen atom, or one of them represents a hydrogen atom and the other represents a saturated or unsaturated alkyl group that may have a substituent. The alkyl group of $R_1$ or $R_2$ is preferably an alkyl group having a small number of carbons, and examples include a methyl group, an ethyl group, and a 2-hydroxyethyl group.

In addition, $R_3$, $R_4$, and $R_5$ all represent a hydrogen atom, two of them represent a hydrogen atom and the other one represents a saturated or unsaturated alkyl group that may have a substituent, or all of them represent a saturated or unsaturated alkyl group that may have a substituent. The alkyl groups may be of identical or different types, and are linear or cyclic, may have a branched chain, and two groups may be bonded to form a ring.

Examples of the aminium having an ethylenediamine backbone represented by Formula 1 above include 2-aminoethylaminium and 2-(N-hydroxyethylamino)ethylaminium below.

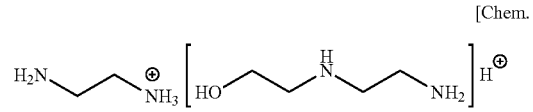

[Chem. 2]

In addition, the propylenediamine backbone is formed by replacing the ethylene group of the ethylenediamine backbone described above by a propylene group. Specifically, the propylenediamine backbone is formed by replacing the ethylene group of Formula 1 described above by a propylene group. A carbon atom of the propylene group of the propylenediamine backbone may have a substituent, such as an alkyl group or heteroalkyl group having a small number of carbons.

Examples of the aminium having an propylenediamine backbone include 3-aminopropylaminium and 3-(N-methylamino)propylaminium below.

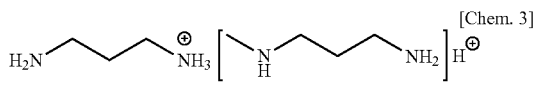

[Chem. 3]

The aminium according to an embodiment of the present invention includes those having two or more ethylenediamine backbones or propylenediamine backbones. For example, an aminium in which either $R_1$ or $R_2$ is an aminoethyl group in Formula 1 above is diethylenetriaminium, and an aminium in which either $R_1$ or $R_2$ is a 2-(aminoethyl)aminoethyl group in Formula 1 above is triethylenetetraaminium. Specifically, examples include 2-(2-(aminoethyl)amino)ethylaminium and 2-(2-(2-(aminoethyl)aminoethyl)amino)ethylaminium below.

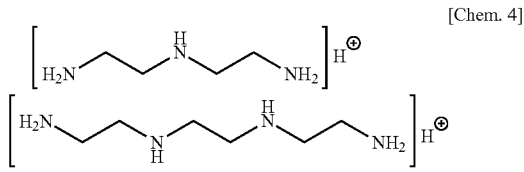

[Chem. 4]

Anion

The anion in the ionic liquid (I) is not particularly limited but is preferably an amide, such as bis(trifluoromethylsulfonyl)amide or dicyanamide; a sulfonate, such as methylsulfonate or trifluoromethylsulfonate; a sulfate, such as methylsulfate or ethylsulfate; a halide ion, such as a fluoride ion, a chloride ion, a bromide ion, or an iodide ion; or a carboxylate, such as trifluoroacetate; and in particular, an amide-based anion, such as bis(trifluoromethylsulfonyl)amide (abbreviated as [$Tf_2N$]), is preferably used.

Examples of the preferred ionic liquid (I) include those described below, and among them, [HDAH][$Tf_2N$] is preferably used.

[Chem. 5]

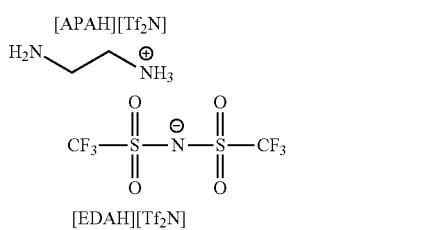

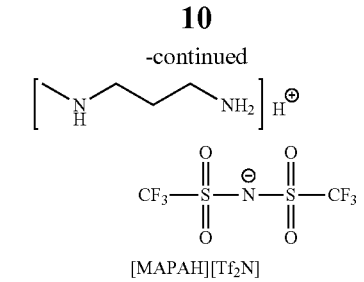

[MAPAH][Tf$_2$N]

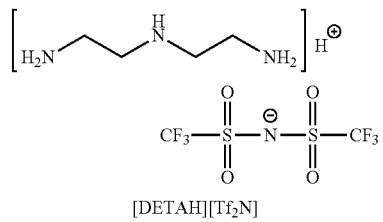

[DETAH][Tf$_2$N]

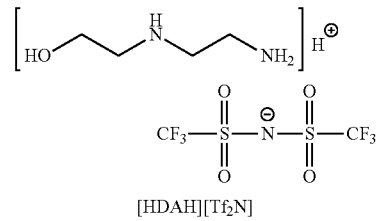

[HDAH][Tf$_2$N]

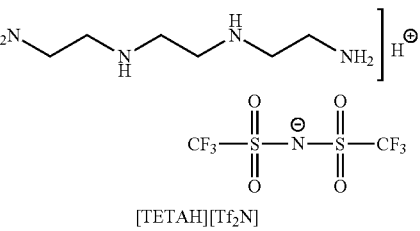

[TETAH][Tf$_2$N]

Ionic Liquid (II)

The ionic liquid (II) in the ionic liquid composition for a carbon dioxide separation membrane according to an embodiment of the present invention is an ionic liquid in which the cation has no primary or secondary amino group, and the anion is an oxoacid anion.

Oxoacid Anion

Examples of the oxoacid anion include carboxylates, such as acetate, propionate, butanoate, and lactate; phosphates, such as dimethyl phosphate, diethylphosphate, and dibutyl phosphate; phosphonates, such as methylphosphonate, ethylphosphonate, and butylphosphonate; sulfates, such as methylsulfate, ethylsulfate, and octylsulfate; and sulfonates, such as methylsulfonate and tosylate. Preferably, the oxoacid anion is one or more selected from the carboxylate, phosphate, and phosphonate shown below.

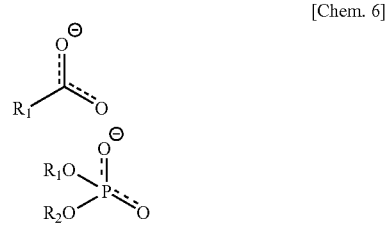

[Chem. 6]

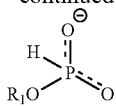

where $R_1$ and $R_2$ represent a saturated or unsaturated alkyl group that is unsubstituted or substituted with a hydroxyl group or a heteroatom.

Examples of the carboxylate particularly preferably used include acetate (abbreviated as [AcO]) and 2-(1-methoxyethoxy)propionate (abbreviated as [1O2OPrO]), and examples of the phosphonate particularly preferably used include methylphosphonate (abbreviated as [MeHPO$_3$]).

Cation

The cation in the ionic liquid (II) according to an embodiment of the present invention is any cation having no primary or secondary amino group and is not particularly limited, and examples include imidazoliums, such as 1-ethyl-3-methylimidazolium, 1-butyl-3-methylimidazolium, 1-hexyl-3-methylimidazolium, 1-octyl-3-methylimidazolium; ammoniums, such as N-butyl-N,N,N,-trimethylammonium, N,N,N,N,-tetrabutylammonium, N-(2-hydroxyethyl)-N,N,N,-trimethylammonium, N,N-diethyl-N-methyl-N-heptylammonium, and N,N-diethyl-N-methyl-N-(6-hydroxyhexyl)ammonium; pyridiniums, such as N-methylpyridinium, N-ethylpyridinium, and N-butylpyridinium; pyrrolidinium, such as N,N-dimethylpyrrolidinium, N-methyl-N-ethylpyrrolidinium, and N-methyl-N-butylpyrrolidinium; and phosphoniums, such as tetrabutylphosphonium, triethyloctylphosphonium, tributyloctylphosphonium, and trihexyltetradecylphosphonium. In particular, an imidazolium having an alkyl group in the side chain, such as 1,3-dialkylimidazolium, is preferably used.

In dialkylimidazolium having an alkyl group in the side chain, shortening the alkyl group in the side chain reduces the gas solubility due to physical absorption, and this improves the selectivity ratio for nitrogen or the like (see Comparative Examples 3 and 4 described later). Thus, 1-ethyl-3-methylimidazolium (abbreviated as [emim]) is particularly preferably used.

Examples of the representative ionic liquid (II) include ionic liquids below.

[Chem. 7]

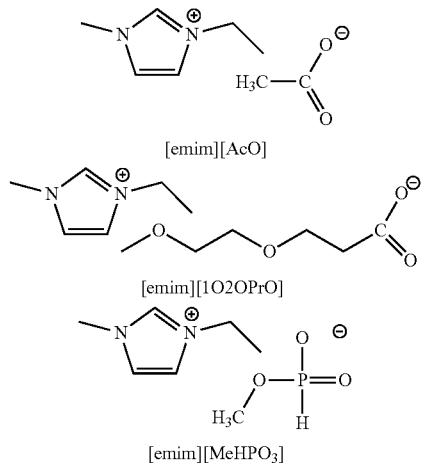

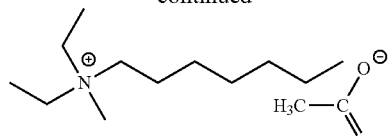

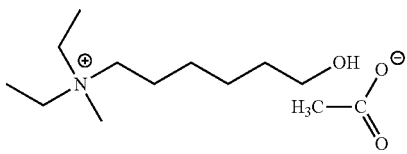

Ratios of Both Ionic Liquids

The mixing ratios of both ionic liquids preferred to improve the permeation selectivity of carbon dioxide vary depending on the combination of both ionic liquids.

For example, when the ionic liquid (I) is [HDAH][Tf$_2$N] and the ionic liquid (II) is [emim][AcO], the ionic liquid (I) can improve the permeation selectivity ratio in the range from 5 to 40 mol % relative to the total of both ionic liquids.

In addition, when the ionic liquid (I) is [HDAH][Tf$_2$N] and the ionic liquid (II) is [emim][MeHPO$_3$], the ionic liquid (I) can improve the permeation selectivity ratio in the range from 5 to 80 mol % relative to the total of both ionic liquids.

Carbon Dioxide Separation Membrane

The carbon dioxide separation membrane in an embodiment of the present invention is any of those that can retain the ionic liquid composition for carbon dioxide separation (hereinafter referred to simply as the "ionic liquid composition") and is not particularly limited. For example, in the carbon dioxide separation membrane having a porous layer, the ionic liquid composition is retained in voids in the porous layer by impregnating the membrane with the ionic liquid composition, for example.

In addition, for the carbon dioxide separation membrane having a porous layer containing an inorganic material microparticle, the ionic liquid composition is retained in voids in the porous layer by impregnating the membrane with the ionic liquid composition likewise, for example.

Examples of the preferred carbon dioxide separation membrane include an ionic liquid affinitive porous layer (C) retaining an ionic liquid composition liquid (A) in voids, and an ionic liquid non-affinitive porous layer (B).

The ionic liquid affinitive porous layer (C) may contain an inorganic material, for example, metal oxide particles with an average particle size from 0.001 to 5 μm on a number basis).

In addition, the average thickness of the ionic liquid affinitive porous layer (C) is preferably from 0.01 to 10 μm.

Each layer will be described below.

Ionic Liquid Non-Affinitive Porous Layer (B)

The ionic liquid non-affinitive porous layer (B) has many pores (micropores or voids) inside, and the surfaces of this layer (which may include the surfaces (or wall surfaces) of the internal voids) are generally hydrophobic (relatively hydrophobic compared with the ionic liquid affinitive porous layer (C)). In addition, the voids may or may not include an independent pore but includes at least a communication pore (or a through pore) that communicates in the thickness direction. The ionic liquid non-affinitive porous layer (B) (material constituting the ionic liquid non-affinitive porous layer (B) or formation component of the ionic liquid non-affinitive porous layer (B)) may contain a resin (e.g., thermoplastic resin) as a main component [e.g., at 50 wt. % or greater, preferably 70 wt. % or greater, and more preferably 90 wt. % or greater (substantially 100 wt. %) relative to the weight of the entire ionic liquid non-affinitive porous layer (B)]. From the viewpoint of excellent formability and the like, the ionic liquid non-affinitive porous layer (B) is generally a porous membrane (porose membrane, porosity membrane, or microporous membrane) formed of a thermoplastic resin.

Examples of the thermoplastic resin include polyolefin-based resins, polyester-based resins (e.g., poly(alkylene arylate) resins, such as poly(ethylene terephthalate), poly(butylene terephthalate), and poly(ethylene naphthalate)), polycarbonate-based resins (e.g., bisphenol type polycarbonate resins, such as bisphenol A type polycarbonate resins, bisphenol F type polycarbonate resins, and bisphenol S type polycarbonate resins), polyamide-based resins (e.g., aliphatic polyamide resins, such as polyamide 6 and polyamide 66), polysulfone-based resins (e.g., polysulfone and polyethersulfone), fluororesins, and cellulose derivatives.

These thermoplastic resins can be used alone or in combination of two or more.

Of these, the thermoplastic resin is preferably a polyolefin-based resin, a fluororesin, or a cellulose derivative (particularly a polyolefin-based resin or a fluororesin; and from the viewpoint of easy availability, a polyolefin-based resin) and particularly a poly α-C2-3 olefin resin, such as a polyethylene-based resin or a polypropylene-based resin (particularly a polyethylene-based resin) or a fluororesin, such as PTFE or PVDF (particularly PVDF).

These thermoplastic resins may contain an additive commonly used in the art. Examples of the additive commonly used in the art include stabilizers, such as heat stabilizers, antioxidants, and ultraviolet absorbers; preservatives; bactericides; plasticizers; lubricants; colorants; viscosity modifiers; leveling agents; surfactants; and antistatic agents. These additives can be used alone or in combination of two or more. The ratio of the additive is, for example, 50 parts by weight or less, preferably 30 parts by weight or less (e.g., from 0.01 to 30 parts by weight) and more preferably 10 parts by weight or less (e.g., from 0.1 to 10 parts by weight) per 100 parts by weight of the resin.

The method for preparing a porous membrane of such a thermoplastic resin is not particularly limited, and the porous membrane may be prepared by a method commonly used in the art, such as a method in which a phase separation of a resin solution is used, a method in which a resin film is subjected to a stretching process, or a method in which a resin film is irradiated with a high energy ray, such as an a ray.

In addition, the ionic liquid non-affinitive porous layer (B) may be subjected to a surface treatment commonly used in the art (e.g., treatment described in JP 06-009810 A, that is, treatment of depositing a cross-linked product derived from an ethylenically unsaturated monomer having a fluorinated alkyl group) to adjust wettability (or a contact angle) to the ionic liquid composition (A).

For the ionic liquid non-affinitive porous layer (B), a commercially available product may be used, and examples include "CPORE" available from Ube Maxell Co., Ltd., "UPORE" available from Ube Industries, Ltd., and "Durapel" available from Merck Millipore.

The average thickness of the ionic liquid non-affinitive porous layer (B) may be, for example, from 1 to 200 μm, preferably from 5 to 150 μm, and more preferably from 10 to 130 μm.

The pore diameter (average pore diameter or average micropore diameter) of the ionic liquid non-affinitive porous layer (B) may be selected from a wide range, for example, from 0.001 to 10 μm (e.g., from 0.01 to 5 μm) and may be, for example, from 0.001 to 1 μm (e.g., from 0.005 to 0.5 μm), preferably from 0.01 to 0.4 μm (e.g., from 0.03 to 0.35 μm), and more preferably from 0.05 to 0.3 μm (e.g., from 0.07 to 0.25 μm). With an extremely small pore diameter, the gas permeability would decrease, and with an extremely large pore diameter, the ionic liquid composition (A) or the like would permeate through and fail to be retained in the carbon dioxide separation membrane (ionic liquid-containing laminate). In the present specification and claims, the pore diameter (average pore diameter or average micropore diameter) can be measured by a method, such as mercury porosimetry, commonly used in the art.

The porosity of the ionic liquid non-affinitive porous layer (B) may be selected from a wide range, for example, from 1 to 90% (e.g., from 10 to 80%) according to the method for producing the porous layer or the like and may be, for example, from 20 to 85%, preferably from 30 to 80%, and more preferably from 40 to 75%. With an extremely small porosity, the gas permeability would decrease, and with an extremely large pore diameter, the ionic liquid composition (A) would permeate through and fail to be retained in the carbon dioxide separation membrane (ionic liquid-containing laminate). In the present specification and claims, the porosity (void content) represents a volume ratio of voids in the porous layer to the volume of the entire porous layer of either one (the entire ionic liquid non-affinitive porous layer (B) or the entire ionic liquid affinitive porous layer (C)) and can be measured by a method described in Examples below.

The communication pore ratio in the ionic liquid non-affinitive porous layer (B) may be, for example, 50% or greater, preferably 70% or greater, and more preferably 90% or greater (e.g., substantially 100%). In the present specification and claims, the communication pore ratio represents the volume ratio of the communication pore to the voids in the porous layer and may be calculated from an image of a cross section observed with a scanning electron microscope (SEM) or the like.

The contact angle of the ionic liquid non-affinitive porous layer (B) to the ionic liquid composition (A) is, for example, 900 or greater (e.g., from 90 to 150°), preferably 95° or greater (e.g., from 95 to 148°), and more preferably 100° or greater (e.g., from 100 to 145°). With an extremely small contact angle, the ionic liquid-containing liquid (A) would permeate through and fail to be retained. In the present specification and claims, the contact angle can be measured by a method commonly used in the art as described above.

Ionic liquid affinitive porous layer (C) (or second porous layer (C)) The ionic liquid affinitive porous layer (C) has many pores (micropores or voids) inside, and the surfaces of this layer (which may include the surfaces (or wall surfaces) of the internal voids) are generally hydrophilic (relatively hydrophilic compared with the ionic liquid non-affinitive porous layer (B)). In addition, the voids may or may not include an independent pore but includes at least a communication pore (or a through pore) that communicates in the thickness direction. The ionic liquid affinitive porous layer (C) (a material constituting the ionic liquid affinitive porous layer (C) or a formation component of the ionic liquid affinitive porous layer (C)] may contain the organic material, such as the resin, described in the section of the ionic liquid non-affinitive porous layer (B) as the main component but, from the viewpoint of excellent formability and mechanical properties, contains an inorganic material as the main component, for example, 50 wt. % or greater, preferably 70 wt. % or greater, and more preferably 90 wt. % or greater (substantially 100 wt. %) relative to the weight of the entire ionic liquid affinitive porous layer (C). Thus, the ionic liquid affinitive porous layer (C) may be a layer formed by hydrophilization of the resin described in the section of the ionic liquid non-affinitive porous layer (B) (e.g., such as a porous membrane made of hydrophilized PTFE or a porous membrane made of hydrophilized PVDF) but is generally a porous membrane (porose membrane, porosity membrane, or microporous membrane) formed of an inorganic material. The ionic liquid affinitive porous layer (C) thus formed of an inorganic material can impart rigidity originating from the inorganic material to the ionic liquid-containing laminate. Thus, the carbon dioxide separation membrane (ionic liquid-containing laminate) is easy to handle even if it is thin, and the handling properties can be effectively improved. In particular, this can not only effectively reduce the swelling or gelation that would otherwise cause a decrease in gas permeability but also improve the dimensional stability; thus, this is preferred.

Examples of the inorganic material generally include metal oxides, for example, oxides of Group 4A metal (e.g., such as titanium oxide and zirconium oxide), oxides of Group 5A metal (such as vanadium oxide), oxides of Group 6A metal (such as molybdenum oxide and tungsten oxide), oxides of Group 7A metal (such as manganese oxide), oxides of Group 8 metal (such as nickel oxide and iron oxide), oxides of Group 1B metal (such as copper oxide), oxides of Group 2B metal (such as zinc oxide), oxides of Group 3B metal (such as aluminum oxide and indium oxide), oxides of Group 4B metal (such as silicon oxide and tin oxide), and oxides of Group 5B metal (such as antimony oxide) of the periodic table.

These metal oxides can be used alone or in combination of two or more. Of these metal oxides, from the viewpoints, such as the affinity (or hydrophilicity) with the ionic liquid composition (A), easy preparation of a dispersion (or slurry) resulting from specific gravity or the like, and furthermore, the ease of availability, the metal oxide is preferably a Group 3B metal oxide, such as aluminum oxide; or a Group 4B metal oxide, such as silicon oxide (particularly a Group 3B metal oxide, such as aluminum oxide).

The inorganic material (or metal oxide) may be in particulate form. The average particle size of the inorganic material (or metal oxide) is, for example, from 0.001 to 10 µm (e.g., from 0.01 to 5 µm), preferably from 0.1 to 3 µm (e.g., from 0.3 to 2 µm), and more preferably from 0.5 to 1.5 µm (e.g., from 0.8 to 1.2 µm) on a number basis. In the present specification and claims, the average particle size can be measured by a method described in Examples below.

The shape of the particle is not particularly limited, and examples include spherical (or nearly spherical), ellipsoidal, polyhedral (such as polygonal pyramid, cube, and rectangular parallelepiped), plate, rod, and an indefinite shape, but the shape is usually an indefinite shape. In addition, the inorganic material may or may not be surface-treated from the viewpoint of improving dispersibility.

Preparation of the ionic liquid affinitive porous layer (C) using a particulate inorganic material (or metal oxide) can adjust the gas permeability of the ionic liquid affinitive porous layer (C) itself at a high level due to the gaps (voids) between the particles and thus can effectively prevent the decrease in gas permeability also in a laminated structure. In addition, even through the surface of the carbon dioxide separation membrane (e.g., the ionic liquid affinitive porous layer (C) side in the carbon dioxide separation membrane) is contacted, it is less likely to exude the ionic liquid-containing liquid (A) contained inside probably because of the rigidity of the ionic liquid affinitive porous layer (C). Thus, it is likely to retain the ionic liquid composition (A) stably in the liquid state as is and seems to be able to effectively reduce the stickiness of the carbon dioxide separation membrane (ionic liquid-containing laminate) surface.

In addition, the ionic liquid affinitive porous layer (C) may be subjected to a surface treatment commonly used in the art (e.g., such as treatment using a silane coupling agent) to adjust wettability (or contact angle) to the ionic liquid composition (A).

The average thickness of the ionic liquid affinitive porous layer (C) can be selected from the range, for example, from 0.01 to 100 µm (e.g., from 0.03 to 70 µm) and may be, for example, from 0.05 to 50 µm (e.g., from 0.1 to 30 µm), preferably from 0.5 to 20 µm (e.g., from 1 to 15 µm), and more preferably from 1 to 10 µm (e.g., from 2 to 7 µm). With an excessively large average thickness, the weight of the carbon dioxide separation membrane (ionic liquid-containing laminate) would increase.

The pore diameter (average pore diameter or average micropore diameter) of the ionic liquid affinitive porous layer (C) may be, for example, from 0.001 to 10 µm (e.g., from 0.01 to 5 µm). With an extremely small pore diameter, not only the amount of ionic liquid composition (A) that can be retained would decrease but also the gas permeability would decrease. When the ionic liquid affinitive porous layer (C) is formed of an inorganic material (e.g., such as a metal oxide particle), it seems to easily adjust the gas permeability at a high level.

The porosity (void content) of the ionic liquid affinitive porous layer (C) may be selected from a wide range, for example, from 1 to 90% (e.g., from 10 to 80%) and may be, for example, from 5 to 70% (e.g., from 10 to 60%), preferably from 15 to 50% (e.g., from 20 to 45%), and more preferably from 25 to 40% (e.g., from 30 to 35%). With an extremely low porosity, not only the amount of ionic liquid composition (A) that can be retained would decrease, but also the gas permeability would decrease. With an extremely high porosity, the ionic liquid-containing liquid (A) would not be stably retained.

The communication pore ratio in the ionic liquid affinitive porous layer (C) may be, for example, 50% or greater, preferably 70% or greater, and more preferably 90% or greater (e.g., substantially 100%).

The contact angle of the ionic liquid affinitive porous layer (C) to the ionic liquid composition (A) may be, for example, less than 900 (e.g., 0° or greater and less than 90°), preferably 850 or less (e.g., from 15 to 85°), and more preferably 80° or less (e.g., from 30 to 80°). With an excessively large contact angle, the retention of the ionic liquid composition (A) would be difficult.

The difference between the contact angles of the ionic liquid non-affinitive porous layer (B) and the ionic liquid affinitive porous layer (C) to the ionic liquid composition (A) is, for example, 100 or greater (e.g., from 15 to 55°), preferably 200 or greater (e.g., from 25 to 50°), and more preferably 300 or greater (e.g., from 30 to 45°). With an extremely small difference between the contact angles, the stable retention of the ionic liquid composition (A) would be difficult. In addition, with an extremely large difference between the contact angles, the ionic liquid composition (A) would not spread in a flat shape (or in the surface direction) inside the ionic liquid affinitive porous layer when the basis weight of the ionic liquid composition (A) is small.

Carbon Dioxide Separation Membrane (Ionic Liquid-Containing Laminate) and Method for Producing Same The carbon dioxide separation membrane (ionic liquid-containing laminate) according to an embodiment of the present invention may include impregnating a liquid (or impregnation liquid) containing the ionic liquid composition (A) into voids in the ionic liquid affinitive porous layer (C) in a laminate (ionic liquid-free laminate) including the ionic liquid non-affinitive porous layer (B) and the ionic liquid affinitive porous layer (C) (impregnation).

The impregnation liquid may be composed only of the ionic liquid composition (A) or may be a mixed liquid (solution or dispersion) prepared by mixing the ionic liquid composition (A) and a solvent (or a dispersion medium). From the viewpoint of easily reducing the equivalent membrane thickness of the ionic liquid composition (A), the impregnation liquid is preferably a mixed liquid. In the present specification and claims, the "equivalent membrane thickness" means a membrane thickness of the liquid membrane when the liquid membrane having the same area as that of the carbon dioxide separation membrane (ionic liquid-containing laminate) is prepared using the ionic liquid composition (A) to be contained in the porous layer.

The solvent (or dispersion medium) is preferably a solvent with higher volatility than that of the ionic liquid composition (A), and examples include water, alcohols (lower alcohols, such as methanol, ethanol, isopropanol, butanol, and cyclohexanol), ketones (such as acetone, methyl ethyl ketone, methyl isobutyl ketone, and cyclohexanone), esters (such as methyl acetate, ethyl acetate, propyl acetate, butyl acetate, methyl formate, and ethyl formate), ethers (such as diethyl ether, dioxane, and tetrahydrofuran), aliphatic hydrocarbons (such as hexane), alicyclic hydrocarbons (such as cyclohexane), aromatic hydrocarbons (such as benzene), halogenated hydrocarbons (such as dichloromethane and dichloroethane), cellosolves (such as methyl cellosolve and ethyl cellosolve), cellosolve acetates, and amides (such as dimethylformamide and dimethylacetamide). These solvents can be used alone or in combination of two or more. Of these solvents, an aqueous solvent (or a water-soluble solvent), such as water and an alcohol (e.g., a C2-6 alkanol, such as methanol), is usually used. The concentration of the ionic liquid composition (A) in the impregnation liquid is, for example, from 0.001 to 100 wt. %, preferably from 0.01 to 50 wt. % (e.g., from 0.05 to 30 wt. %), and more preferably from 0.1 to 10 wt. % (e.g., from 0.1 to 8 wt. %).

The method for impregnating the impregnation liquid is not particularly limited and may be, for example, a method in which the impregnation liquid is injected under pressure. Specifically, the impregnation liquid may be impregnated by a method in which the laminate surface (or the outermost layer of the laminate) on the ionic liquid affinitive porous layer (C) side in the laminate (ionic liquid-free laminate) including the ionic liquid non-affinitive porous layer (B) and the ionic liquid affinitive porous layer (C) is brought into contact with the impregnation liquid, and a pressure on the opposite side (ionic liquid non-affinitive porous layer (B) side) is reduced (or suction is performed from the opposite side). Such a method can easily or efficiently form the carbon dioxide separation membrane (ionic liquid-containing laminate) according to an embodiment of the present invention.

In addition, when the mixed liquid is used as the impregnation liquid, the carbon dioxide separation membrane (ionic liquid-containing laminate) may be prepared by volatilizing the solvent (or dispersion medium) after the impregnation. Removal of the solvent (or dispersion medium) enables the equivalent membrane thickness of the ionic liquid-containing liquid (A) to be easily adjusted and facilitates the reduction in the membrane thickness. The method for volatilizing the solvent is not particularly limited, and the solvent is volatilized by appropriately heating and/or reducing the pressure according to the boiling point or vapor pressure of the solvent.

The carbon dioxide separation membrane (ionic liquid-containing laminate) according to an embodiment of the present invention preferably does not contain the ionic liquid composition (A) in a content exceeding 100 parts by volume per 100 parts by volume of the voids inside the ionic liquid affinitive porous layer (C). That is, the carbon dioxide separation membrane (ionic liquid-containing laminate) preferably does not have a second ionic liquid-containing layer that is adjacent to the ionic liquid affinitive porous layer (C) containing (or retaining) the ionic liquid composition (A) and contains the ionic liquid composition (A) in an amount that the voids fail to retain. Thus, from the viewpoint of being able to improve the carbon dioxide permeation rate and handling properties of the carbon dioxide separation membrane (ionic liquid-containing laminate), the ionic liquid affinitive porous layer (C) may contain the ionic liquid composition (A) in a volume that can be selected from the range of 100 parts by volume or less, for example, from 0.1 to 99 parts by volume (e.g., from 1 to 90 parts by volume), for example, from 3 to 80 parts by volume (e.g., from 5 to 70 parts by volume), preferably from 10 to 50 parts by volume (e.g., from 15 to 45 parts by volume), and more preferably from 20 to 40 parts by volume (e.g., from 25 to 35 parts by volume) per 100 parts by volume of the internal voids. With an excessive amount of ionic liquid composition (A), the handling properties would be impaired.

In the carbon dioxide separation membrane (ionic liquid-containing laminate) according to an embodiment of the present invention, the equivalent membrane thickness of the ionic liquid composition (A) is, for example, from 0.01 to 5 μm, (e.g., from 0.05 to 3 μm), preferably from 0.1 to 2 μm (e.g., from 0.15 to 1.5 μm), and more preferably from 0.2 to 1 μm (e.g., from 0.2 to 0.7 μm). With an excessively large equivalent membrane thickness, the permeation rate would decrease.

The laminate (ionic liquid-free laminate) including the ionic liquid non-affinitive porous layer (B) and the ionic liquid affinitive porous layer (C) can be prepared, for example, by directly or indirectly laminating (or forming) the ionic liquid affinitive porous layer (C) on either surface of the ionic liquid non-affinitive porous layer (B). The method for laminating (or forming) the ionic liquid affinitive porous layer (C) is not particularly limited and may be, for example, pressure bonding, heat fusion, and adhesion with an adhesive or a pressure sensitive adhesive. In addition, when the ionic liquid affinitive porous layer (C) is formed of an inorganic material, the ionic liquid affinitive porous layer (C) may be formed by a method commonly used in the art, for example, a method of sintering a powdery inorganic material. However, from the viewpoint of being able to easily or efficiently form a predetermined porous layer and improve the handling properties, the ionic liquid affinitive porous layer (C) may be formed by a method including coating with a dispersion (or slurry) prepared by dispersing a particulate (or powdery) inorganic material in a dispersion medium, and drying the coating.

Examples of the dispersion medium include those similar to the solvents (or dispersion media) exemplified in the section of the impregnation liquid. These dispersion media can be used alone or in combination of two or more. Of these dispersion media, water is usually used. When water is used as the dispersion medium, an alcohol, such as isopropanol, may be added in a small amount (e.g., from 0.01 to 10 parts by weight and preferably from 0.1 to 2 parts by weight per 100 parts by weight of the inorganic material) as necessary to improve the coating properties for the ionic liquid non-affinitive porous layer (B).

In addition, as necessary, a binding agent (or binder) [e.g., a water-soluble resin, such as carboxymethyl cellulose or its salt (such as sodium salt), hydroxyalkyl cellulose (such as hydroxyethyl cellulose or hydroxypropyl cellulose), or methyl cellulose; latex, such as styrene butadiene rubber latex] may be added in a small amount (e.g., from 0.01 to 10 parts by weight and preferably from 0.1 to 2 parts by weight per 100 parts by weight of the inorganic material). Although the binding agent is not always necessary, this often enables easy preparation of the ionic liquid affinitive porous layer (C) with a large membrane thickness.

The concentration of the inorganic material in the dispersion is, for example, from 0.1 to 50 wt. %, preferably from 1 to 30 wt. %, and more preferably from 3 to 20 wt. % (e.g., from 5 to 15 wt. %) relative to the weight of the entire dispersion.

The coating method is not particularly limited, and examples include methods commonly used in the art, such as a roll coater method, an air knife coater method, a blade coater method, a rod coater method, a reverse coater method, a bar coater method, a comma coater method, a dip-squeeze coater method, a die coater method, a gravure coater method, a micro gravure coater method, a silk screen coater method, a dip method, a spray method, and a spinner method. Of these methods, the bar coater method is widely used. If necessary, the dispersion (or coating liquid) may be applied for coating multiple times.

In the coating, the dispersion is further flow-cast or applied for coating, and then the dispersion medium is evaporated to dry the coating. The drying temperature can usually be selected according to the boiling point of the dispersion medium or the like and may be, for example, from 50 to 150° C., preferably from 80 to 120° C., and more preferably from 90 to 110° C.

The carbon dioxide separation membrane (or ionic liquid-free laminate including the ionic liquid non-affinitive porous layer (B) and the ionic liquid affinitive porous layer (C)) according to an embodiment of the present invention may have a two-layer structure of the ionic liquid non-affinitive porous layer (B) and the ionic liquid affinitive porous layer (C), and furthermore may have a multilayer structure (e.g., three to five-layer structure) of three or more layers including another layer (or a third layer), such as the support layer. The third layer is not particularly limited as long as gas can permeate the layer, and examples include the support layer [e.g., such as a net (or mesh) made of metal (such as stainless steel) or resin] and an adhesive or pressure sensitive adhesive layer. These third layers may be used alone or in combination of two or more types. From the viewpoint of the gas permeability, the carbon dioxide separation membrane (ionic liquid-containing laminate) according to an embodiment of the present invention preferably has a two or three-layer structure (particularly a two-layer structure). In addition, from the viewpoint of being able to effectively retain or fix the ionic liquid composition (A), the ionic liquid non-affinitive porous layer (B) and the ionic liquid affinitive porous layer (C) are preferably formed adjacent to each other.

The carbon dioxide separation membrane (ionic liquid-containing laminate) according to an embodiment of the present invention thus obtained has excellent gas permeability and thus can be suitably used, for example, as a carbon dioxide separation membrane (carbon dioxide concentration membrane) for fertilization for plants in the agricultural field. The carbon dioxide separation membrane according to an embodiment of the present invention is usually used by setting the side of the ionic liquid affinitive porous layer (C) containing the ionic liquid composition (A) as a gas feed side (feed side or upstream side) and the opposite side (ionic liquid non-affinitive porous layer (B) side) as a permeating side (or downstream side).

The carbon dioxide permeability coefficient, the nitrogen permeability coefficient, and the carbon dioxide selectivity ratio can be measured by a method described in Examples below or the like.

Carbon Dioxide Concentration Apparatus Provided with Carbon Dioxide Separation Membrane A carbon dioxide concentration apparatus according to an embodiment of the present invention is provided with the carbon dioxide separation membrane. The shape of the carbon dioxide separation membrane is not particularly limited and may be, for example, a flat membrane shape, a spiral shape formed by winding a flat membrane, or a hollow fiber membrane shape. These shapes can be used alone or in combination of two or more. For the carbon dioxide separation membrane, a membrane module (concentration unit or separation unit) is usually formed together with a support material for supporting or fixing the carbon dioxide separation membrane. The material and shape of the support material are not particularly limited as long as they do not inhibit gas permeation, and are appropriately selected according to the shape or the like of the carbon dioxide separation membrane. In addition, the concentration unit may include one carbon dioxide separation membrane or may include two or more multiple carbon dioxide separation membranes.

In addition to the concentration unit, the carbon dioxide concentration apparatus is often further provided with an intake unit for feeding a gas component containing carbon dioxide (e.g., such as the atmosphere) to the carbon dioxide separation membrane. The intake unit can feed a gas component containing carbon dioxide to the carbon dioxide separation membrane by generating a pressure difference between the upstream side (or gas feed side) and the downstream side (permeating side) of the concentration unit. The intake unit is not particularly limited as long as it can generate the pressure difference and may be located upstream or downstream in the concentration unit. Specifically, the intake unit may be, for example, an air compressor located upstream in the concentration unit, a pump (e.g., such as a diaphragm pump) located downstream in the concentration unit, or the like.

The carbon dioxide concentration apparatus according to an embodiment of the present invention can be operated (or run) as long as it includes at least the concentration unit and the intake unit. Thus, this can simplify the device configuration (or design) and facilitates the size reduction. In addition, the carbon dioxide concentration membrane has high permeation rate (carbon dioxide permeation rate) and thus can effectively or efficiently concentrate (or enrich) carbon dioxide even at a relatively low pressure difference. Thus, even a small intake unit with low intake capacity can operate smoothly.

EXAMPLES

The present invention will be described below in detail based on examples and comparative examples.

Although the description will be focused on the separation of carbon dioxide with a low partial pressure, the examples show suitable examples of the present invention, and the examples do not limit in any way the application of the present invention to the separation of carbon dioxide with a high partial pressure.

Method for Preparing Carbon Dioxide Separation Membrane

The carbon dioxide separation membrane (hereinafter described as a "$CO_2$ separation membrane") was prepared by the following method.

A hydrophilized PTFE filter (available from Merck Millipore) used as a substrate was washed with ethanol, acetone, and ultrapure water, and then the filter was dried using a vacuum dryer under reduced pressure at 70° C. for 12 hours. A predetermined amount of the ionic liquid was added dropwise to the PTFE filter. The PTFE filter was subjected to vacuuming with a vacuum pump for 12 hours while being heated to 40° C. and was impregnated with the ionic liquid. Excessive ionic liquid was wiped off from the filter so that the ionic liquid occupied from 95 to 100% of the void volume of the filter, and this filter was used as the $CO_2$ separation membrane. The $CO_2$ separation membrane using an alumina-coated filter (available from Daicel Corporation) or a titania-coated filter (available from Daicel Corporation) as the substrate was also prepared in the same manner.

Evaluation Method for Carbon Dioxide Separation Membrane

Figure 1:
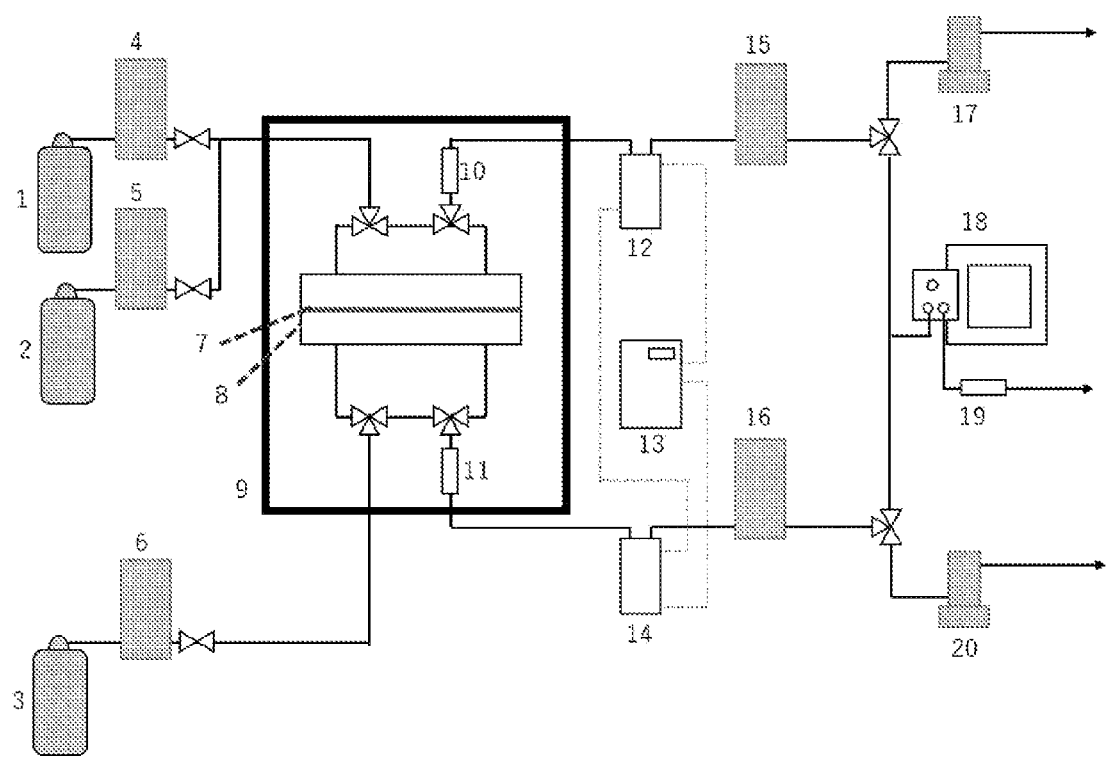
FIG. 1 is a diagram schematically illustrating a device used to measure a $CO_2$ permeability coefficient and $N_2$ permeability coefficient of a $CO_2$ separation membrane.

The $CO_2$ permeability coefficient and $N_2$ permeability coefficient of the $CO_2$ separation membrane were determined using an apparatus of FIG. 1.

FIG. 1 illustrates a $CO_2/N_2$ standard gas cylinder 1, a $N_2$ gas cylinder 2, an Ar gas cylinder 3, mass flow controllers 4 to 6, a $CO_2$ separation membrane 7, a separation membrane holder 8, an oven 9, thermo-hygrometers 10 and 11, traps 12 and 14, a chiller 13, back pressure valves 15 and 16, soap film flow meters 17 and 20, a gas chromatograph (TCD-GC) 18, and a $CO_2$ densitometer 19.

First, the $CO_2$ separation membrane 7 was sandwiched between two PTFE filters (available from Advantec) and set in the separation membrane holder 8. After starting temperature control with the oven 9, a $CO_2/N_2$ mixed gas ($CO_2$ composition was 0.04 mol %, 0.10 mol %, 0.50 mol %, or 1.00 mol %) at the atmospheric pressure was fed at a predetermined flow rate to a bypass on the feed side, and highly pure argon (99.99995 mol % or more) at the atmospheric pressure was fed at a predetermined flow rate to a bypass on the permeating side. The feed side gas that passed through the bypass was analyzed by the gas chromatograph (Shimadzu Corporation, GC-8A) 18 and the $CO_2$ densitometer (VAISALA KK, GMP343) 19, and it was confirmed that the $CO_2$ composition of the feed side gas matched the target value (0.04 mol %, 0.10 mol %, 0.50 mol %, or 1.00 mol %). The permeating side gas that passed through the bypass was analyzed by the same method, and it was confirmed that the components other than argon contained in the permeating side gas were not higher than the detection limit. The feed side gas and the permeating side gas were then fed to the separation membrane holder 8, and a gas permeation test was started. The composition of the permeating side gas was analyzed at certain intervals, and when the compositions of $CO_2$ and $N_2$ remained constant for 1 hour or longer, the steady state was deemed to be reached. The feed side gas and the permeating side gas were analyzed with the gas chromatograph 18 and the $CO_2$ densitometer 19, and further, the flow rate of the gases were measured with the soap film flow meters 17 and 20 (Horiba, Ltd., SF-lU). From the $CO_2$ composition, the $N_2$ composition, and the flow rate, the flow rates ($cm^3/s$) of $CO_2$ and $N_2$ that passed through the $CO_2$ separation membrane per unit time were determined. These values were multiplied by the separation membrane thickness (cm), further divided by the separation membrane area ($cm^2$) and the gas partial pressure difference (cmHg) between the feed side and the permeating side, and the $CO_2$ permeability coefficient and the $N_2$ permeability coefficient were obtained. Both in examples and comparative examples, the unit of the permeability coefficient was expressed in Barrer ($cm^3 \cdot cm/cm^2 \cdot s \cdot cmHg \times 10^{10}$). In addition, the $CO_2$ selectivity ratio was determined as the ratio of the $CO_2$ permeability coefficient to the $N_2$ permeability coefficient.

Synthesis of Ionic Liquid

Synthesis Example 1: synthesis of 3-aminopropylaminium bis(trifluoromethylsulfonyl)amide ([APAH][$Tf_2N$])

A solution of bis(trifluoromethylsulfonyl)imide (available from Kanto Chemical Co., Inc., hereinafter $HTf_2N$) in methanol was slowly added dropwise to a solution of 3-aminopropylamine (available from Aldrich) in methanol (methanol was available from Wako Pure Chemical Industries, Ltd.). After completion of the dropwise addition, the mixed solution was stirred at room temperature overnight, and a solution containing [APAH][$Tf_2N$] shown in the following formula in methanol was obtained. Methanol was distilled off under reduced pressure and further vacuum-dried at 50° C. for 30 hours, and [APAH][$Tf_2N$] was obtained.

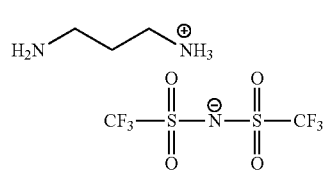

[Chem. 8]

Synthesis Example 2: synthesis of 3-(N-methylamino)propylaminium bis(trifluoromethylsulfonyl)amide ([MAPAH][$Tf_2N$])

[MAPAH][$Tf_2N$] shown in the following formula was obtained in the same manner as in Synthesis Example 1 except that 3-(N-methylamino)propylamine (available from Aldrich) was used in the raw material.

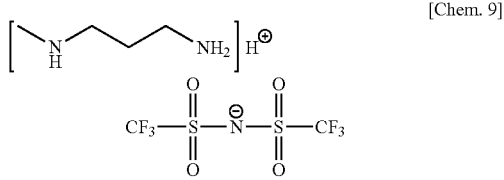

[Chem. 9]

Synthesis Example 3: synthesis of 3-(N,N-dimethylamino)propylaminium bis(trifluoromethylsulfonyl)amide ([DMAPAH][Tf₂N])

[DMAPAH][Tf₂N] shown in the following formula was obtained in the same manner as in Synthesis Example 1 except that 3-(N,N-dimethylamino)propylamine (available from Aldrich) was used in the raw material.

[Chem. 10]

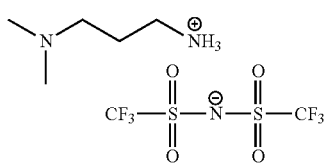

(Synthesis Example 4: synthesis of 2-(N-hydroxyethylamino)ethylaminium bis(trifluoromethylsulfonyl)amide ([HDAH][Tf₂N])

[HDAH][Tf₂N] shown in the following formula was obtained in the same manner as in Synthesis Example 1 except that 2-(N-hydroxyethylamino)ethylamine (available from Aldrich) was used in the raw material.

[Chem. 11]

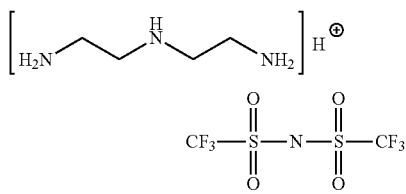

Synthesis Example 5: synthesis of 2-aminoethylaminium bis(trifluoromethylsulfonyl)amide ([EDAH][Tf₂N])

[EDAH][Tf₂N] shown in the following formula was obtained in the same manner as in Synthesis Example 1 except that 2-aminoethylamine (available from Nacalai Tesque, Inc.) was used in the raw material.

[Chem. 12]

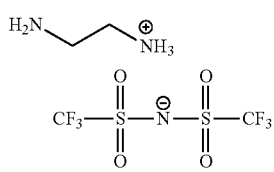

Synthesis Example 6: synthesis of 2-(2-(aminoethyl)amino)ethylaminium bis(trifluoromethylsulfonyl)amide ([DETAH][Tf₂N])

[DETAH][Tf₂N] shown in the following formula was obtained in the same manner as in Synthesis Example 1 except that 2-(2-(aminoethyl)amino)ethylamine (available from TCI) was used in the raw material.

[Chem. 13]

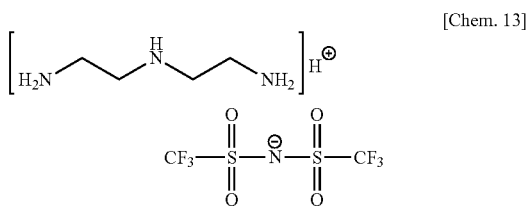

Synthesis Example 7: Synthesis of 2-(2-(2-(aminoethyl)aminoethyl)amino)ethylaminium bis(trifluoromethylsulfonyl)amide ([TETAH][Tf₂N])

[TETAH][Tf₂N] shown in the following formula was obtained in the same manner as in Synthesis Example 1 except that 2-(2-(2-(aminoethyl)aminoethyl)amino)ethylamine (available from Sigma-Aldrich) was used in the raw material.

[Chem. 14]

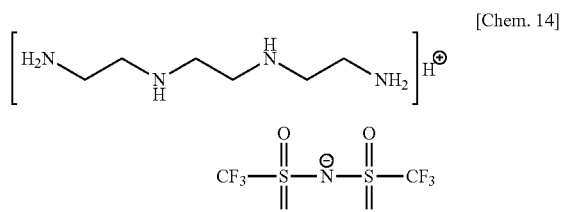

Synthesis Example 8: synthesis of 1-ethyl-3-methylimidazolium 3-(2-methoxyethoxy)propionate ([emim][1O2OPrO])

N-ethylimidazole (available from Sigma-Aldrich), dimethyl carbonate (available from Sigma-Aldrich), methanol (available from Wako Pure Chemical Industries, Ltd.) were reacted at 120° C. for 1 day, and a solution of 1-ethyl-3-methylimidazolium methyl carbonate ([emim][CH₃OCO₂]) in methanol was obtained. The content of [emim][CH₃OCO₂] in the methanol solution was determined with an NMR (Bruker Avance 400). An equivalent amount of 3-(2-methoxyethoxy)propionate (available from Koei Chemical Co., Ltd.) to [emim][CH₃OCO₂] was slowly added dropwise to the [emim][CH₃OCO₂] solution in methanol and then reacted at room temperature for 1 day. To remove an unreacted raw material, distillation under reduced pressure and toluene extraction were then performed, and crude [emim][1O2OPrO] was obtained. Furthermore, the crude [emim][1O2OPrO] was dried under reduced pressure at 40° C. for 1 week to remove a volatile component, and [emim][1O2OPrO] shown in the following formula was obtained.

[Chem. 15]

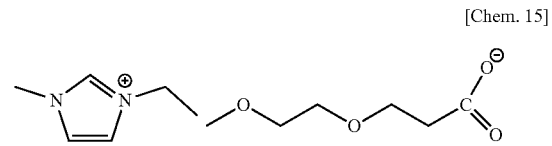

Synthesis Example 9: synthesis of N,N-diethyl-N-methyl-N-heptylammonium acetate ([N$_{1227}$][AcO])

To a solution of N,N-diethyl-N-heptylamine in acetonitrile, iodomethane was added dropwise at 40° C., and the mixture was stirred for 21 hours. The reaction solution was concentrated under reduced pressure, and the concentrate was washed with toluene. The concentrate after washing was dried under reduced pressure, and N,N-diethyl-N-methyl-N-heptylammonium iodide was obtained. This N,N-diethyl-N-methyl-N-heptylammonium iodide was dissolved in methanol, and silver (I) oxide was added in portions. The mixture was stirred at about 25° C. for 12 hours or longer and then filtered. The filtrate was combined with a washing solution resulting from washing the filtration residue with methanol, and a filtrate solution was obtained. To the resulting filtrate solution, acetic acid was added dropwise at about 20° C., and the mixture was stirred. This liquid was concentrated to dryness under reduced pressure, and [N$_{1227}$][AcO] shown in the following formula was obtained.

[Chem. 16]

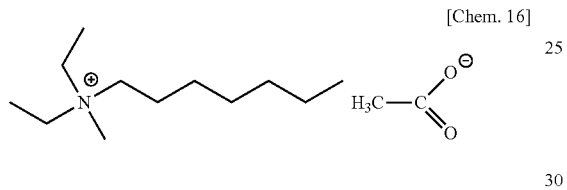

Synthesis Example 10: synthesis of N,N-diethyl-N-methyl-N-(6-hydroxyhexyl)ammonium acetate ([N$_{1226OH}$][AcO])

To a solution of N,N-diethyl-N-(6-hydroxyhexyl)amine in acetonitrile, iodomethane was added dropwise at 40° C., and the mixture was stirred at about 25° C. The reaction solution was concentrated under reduced pressure, and the concentrate was washed with toluene. The concentrate after washing was dried under reduced pressure, and N,N-diethyl-N-methyl-N-(6-hydroxyhexyl)ammonium iodide was obtained. This N,N-diethyl-N-methyl-N-(6-hydroxyhexyl)ammonium iodide was dissolved in methanol, and silver (I) oxide was added in portions. The mixture was stirred at about 25° C. for 12 hours or longer and then filtered. The filtrate was combined with a washing solution resulting from washing the filtration residue with methanol, and a filtrate solution was obtained. To this filtrate solution, silver (I) oxide was added again, and the mixture was stirred and then filtered. To the resulting filtrate solution, acetic acid was added dropwise at about 20° C., and the mixture was stirred. This solution was concentrated to dryness under reduced pressure, and [N$_{1226OH}$][AcO] shown in the following formula was obtained.

[Chem. 17]

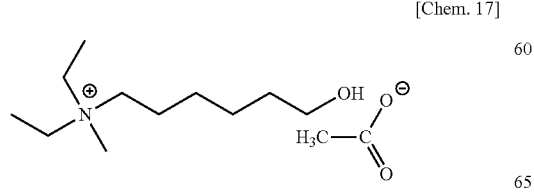

Ionic Liquid Other than Above

In addition to the ionic liquids obtained in Synthesis Examples 1 to 10 described above, the following commercially available ionic liquids were used.

(1) 1-Ethyl-3-methylimidazolium dicyanamide ([emim][DCA] available from Aldrich) shown in the following formula

[Chem. 18]

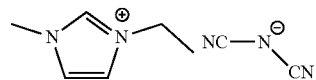

(2) 1-Ethyl-3-methylimidazolium bis(trifluoromethylsulfonyl)amide ([emim][Tf$_2$N] available from Iolitec) shown in the following formula

[Chem. 19]

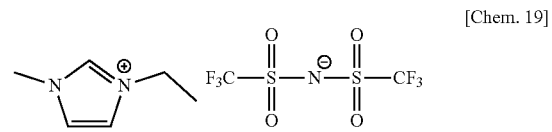

(3) 1-Octyl-3-methylimidazolium bis(trifluoromethylsulfonyl)amide ([omim][Tf$_2$N] available from Iolitec) shown in the following formula

[Chem. 20]

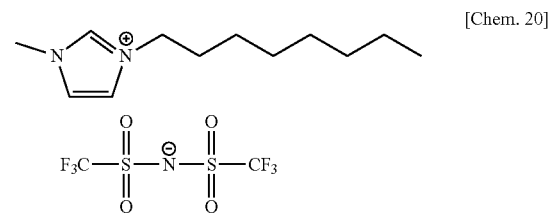

(4) 1-Ethyl-3-methylimidazolium methylphosphonate ([emim][MeHPO$_3$] available from Kanto Chemical Co., Inc.) shown in the following formula

[Chem. 21]

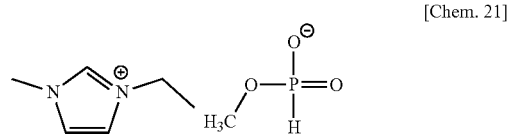

(5) 1-Ethyl-3-methylimidazolium acetate ([emim][AcO] available from Aldrich) shown in the following formula

[Chem. 22]

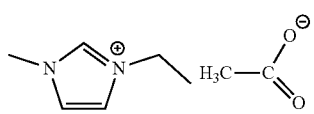

Comparative Examples 1 to 8

A $CO_2$ separation membrane was investigated, which was prepared using a mixed liquid of: an ionic liquid (I) having an aminium having one or more primary or secondary amino groups and an ethylenediamine or propylenediamine backbone; and a diluent in which the anion was $[Tf_2N]$ ([emim][$Tf_2N$] or [omim][$Tf_2N$] described in Patent Document 3 above).

Comparative Example 1

Based on the method for preparing a $CO_2$ separation membrane described above, a $CO_2$ separation membrane in which a hydrophilized PTFE filter was impregnated with 1-ethyl-3-methylimidazolium dicyanamide ([emim][DCA]) was prepared as Comparative Example 1.

Figure 2:
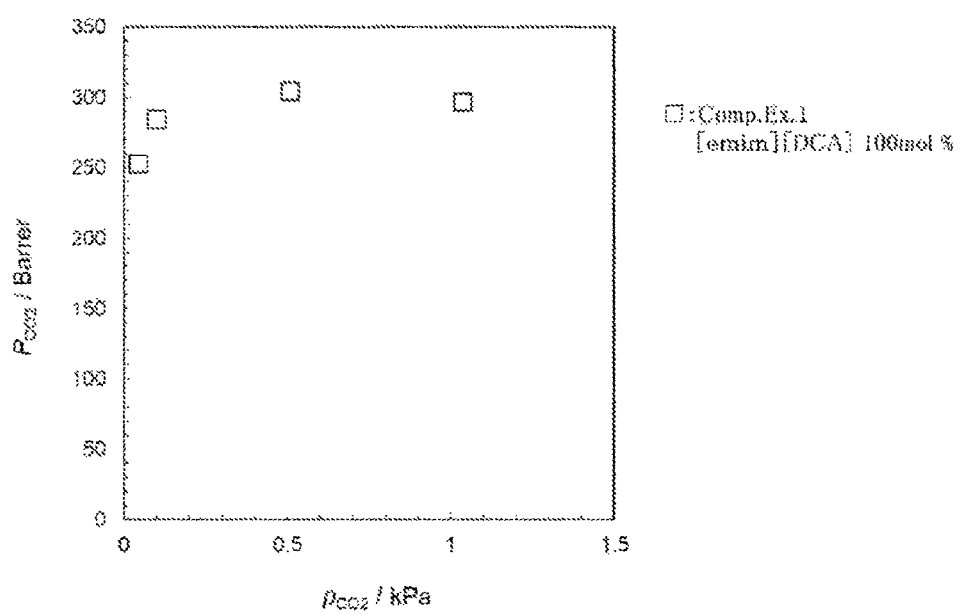
FIG. 2 is a graph showing a partial pressure dependence of a $CO_2$ permeability coefficient of a $CO_2$ separation membrane prepared using [emim][DCA](Comparative Example 1).
Figure 3:
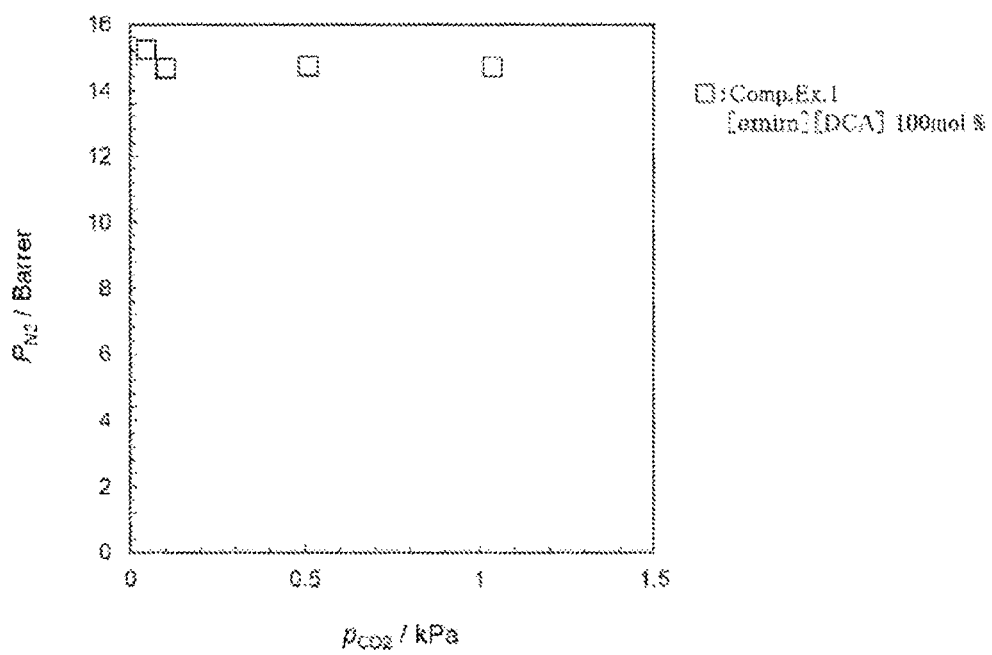
FIG. 3 is a graph showing a partial pressure dependence of a $N_2$ permeability coefficient of the $CO_2$ separation membrane prepared using [emim][DCA](Comparative Example 1).
Figure 4:
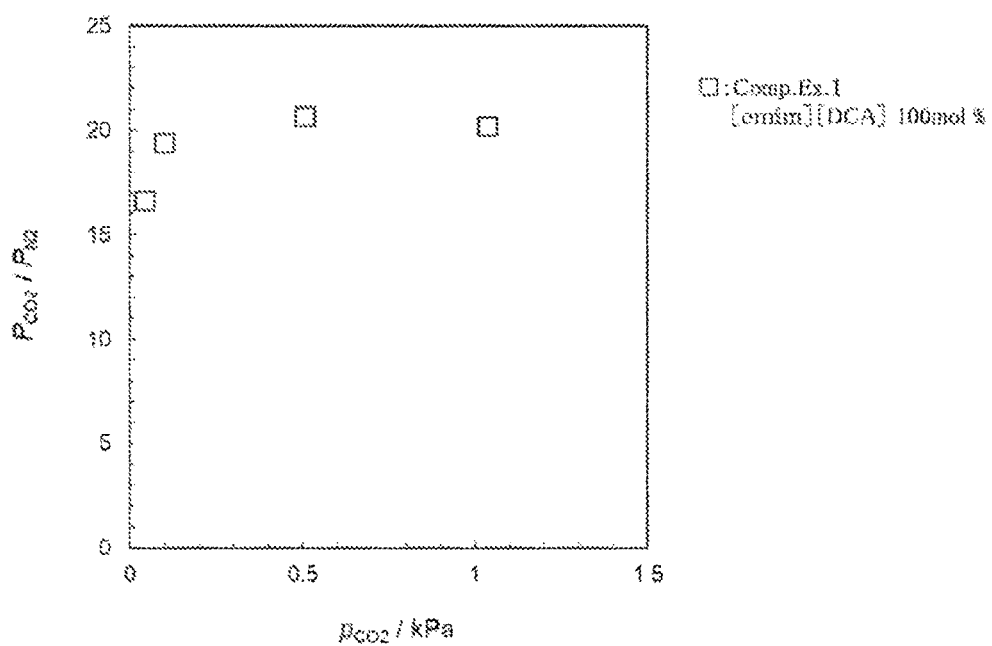
FIG. 4 is a graph showing a partial pressure dependence of a $CO_2$ selectivity ratio of the $CO_2$ separation membrane prepared using [emim][DCA](Comparative Example 1).

The gas permeability coefficients of Comparative Example 1 were measured using four $CO_2/N_2$ mixed gases with different $CO_2$ composition (0.04 mol %, 0.10 mol %, 0.50 mol %, or 1.00 mol %) at a temperature of 40° C., a feed side gas flow rate of 100 mL/min, and a permeating side gas flow rate of 20 mL/min, and the $CO_2$ partial pressure dependences were investigated. The $CO_2$ partial pressure dependences of the resulting $CO_2$ permeability coefficient, $N_2$ permeability coefficient, and $CO_2$ selectivity ratio are shown in FIGS. 2, 3, and 4.

Comparative Example 2

A $CO_2$ separation membrane was prepared as Comparative Example 2 in the same manner as in Comparative Example 1 except that the ionic liquid impregnated into the hydrophilized PTFE filter was changed to an anion 1-ethyl-3-methylimidazolium bis(trifluoromethylsulfonyl)amide ([emim][$Tf_2N$]).

Comparative Examples 3 to 8

$CO_2$ separation membranes were prepared as Comparative Examples 3 to 8 in the same manner as in Comparative Example 1 except that as shown in Table 1 below, a liquid prepared by mixing 3-aminopropylaminium bis(trifluoromethylsulfonyl)amide ([APAH][$Tf_2N$]) obtained in Synthesis Example 1 above, 3-(N-methylamino)propylaminium bis(trifluoromethylsulfonyl)amide ([MAPAH][$Tf_2N$]) obtained in Synthesis Example 2 above, bis(trifluoromethylsulfonyl)amide ([DMAPAH][$Tf_2N$]) obtained in Synthesis Example 3 above, or 2-(N-hydroxyethylamino)ethylaminium bis(trifluoromethylsulfonyl)amide ([HDAH][$Tf_2N$]) obtained in Synthesis Example 4 above, and [emim][$Tf_2N$] above or 1-octyl-3-methylimidazolium bis(trifluoromethylsulfonyl)amide ([omim][$Tf_2N$]) above was used as the ionic liquid impregnated into the hydrophilized PTFE filter.

TABLE 1

| | Ionic liquid (I) | Composition (mol %) of ionic liquid (I) | Diluent |
|---|---|---|---|
| Comparative Example 2 | — | 0 | [emim][$Tf_2N$] |
| Comparative Example 3 | [APAH][$Tf_2N$] | 20 | [emim][$Tf_2N$] |
| Comparative Example 4 | [APAH][$Tf_2N$] | 20 | [omim][$Tf_2N$] |
| Comparative Example 5 | [MAPAH][$Tf_2N$] | 20 | [emim][$Tf_2N$] |
| Comparative Example 6 | [DMAPAH][$Tf_2N$] | 20 | [emim][$Tf_2N$] |
| Comparative Example 7 | [HDAH][$Tf_2N$] | 20 | [emim][$Tf_2N$] |
| Comparative Example 8 | [HDAH][$Tf_2N$] | 100 | — |

The gas coefficients of Comparative Examples 2 to 8 were measured under the same conditions as those in Comparative Example 1, and the $CO_2$ partial pressure dependences were investigated.

Figure 5:
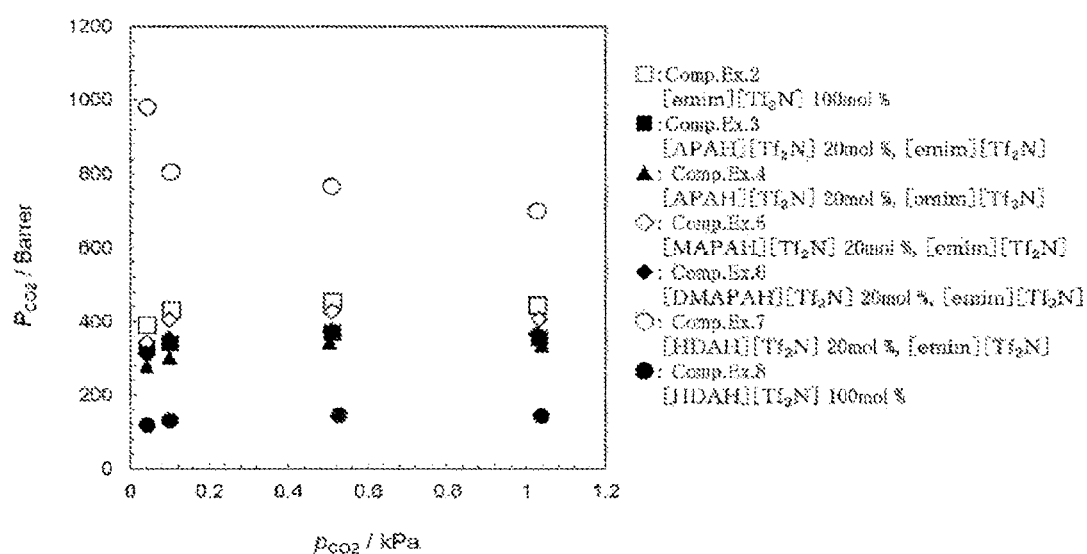
FIG. 5 is a graph showing partial pressure dependences of $CO_2$ permeability coefficients of [emim][$Tf_2N$]-based $CO_2$ separation membranes (Comparative Examples 2 to 8).
Figure 6:
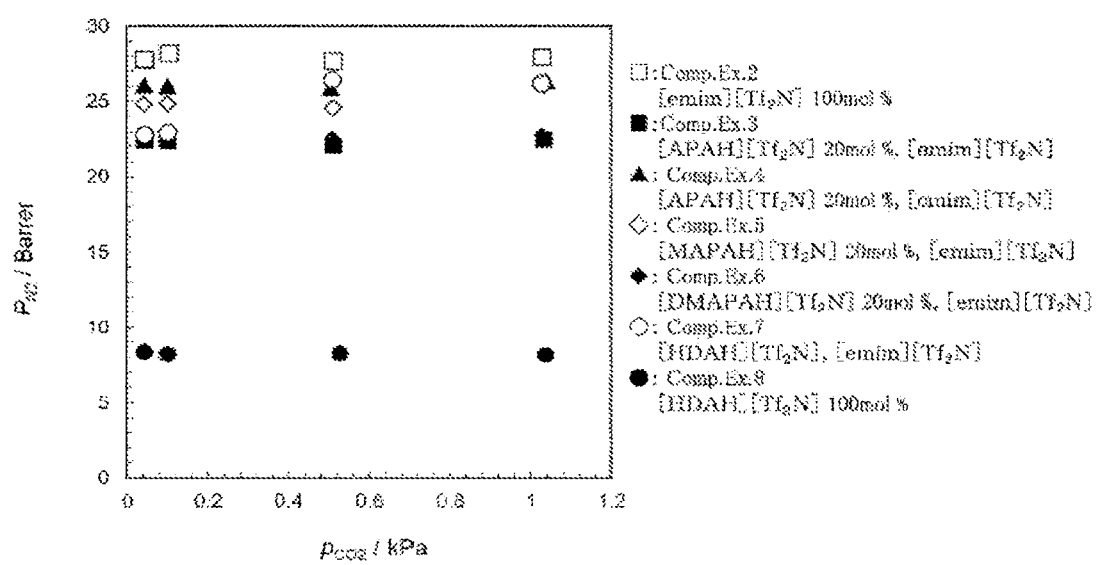
FIG. 6 is a graph showing partial pressure dependences of $N_2$ permeability coefficients of the [emim][$Tf_2N$]-based $CO_2$ separation membranes (Comparative Examples 2 to 8).
Figure 7:
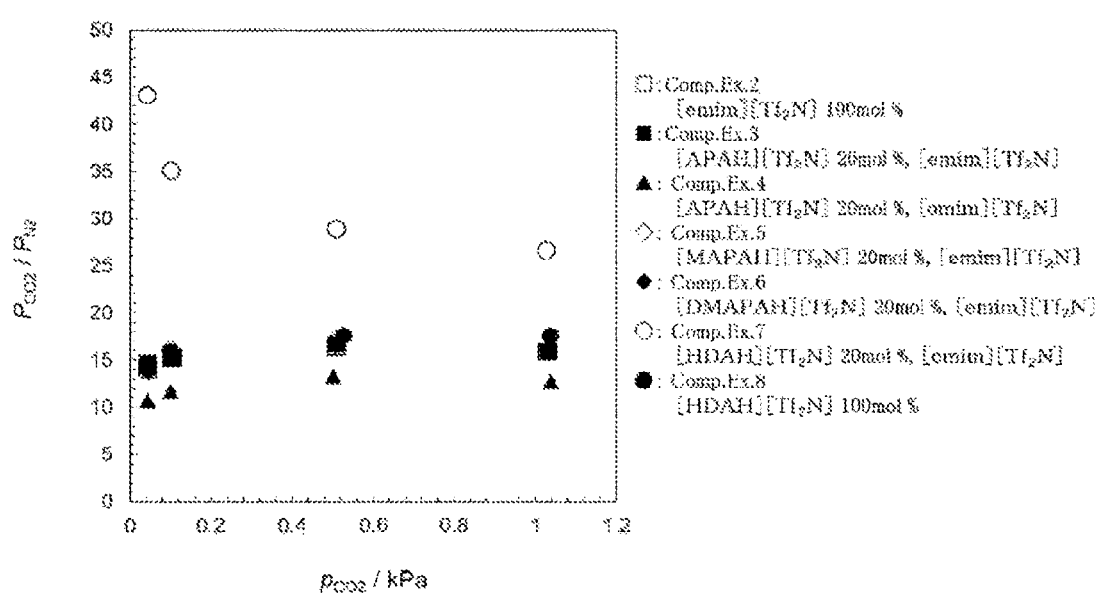
FIG. 7 is a graph showing partial pressure dependences of $CO_2$ selectivity ratios of the [emim][$Tf_2N$]-based $CO_2$ separation membranes (Comparative Examples 2 to 8).

The $CO_2$ partial pressure dependences of the resulting $CO_2$ permeability coefficient, $N_2$ permeability coefficient, and $CO_2$ selectivity ratio are shown in FIGS. 5, 6, and 7,
where □ shows Comparative Example 2, ■ shows Comparative Example 3, ▲ shows Comparative Example 4, ◇ shows Comparative Example 5, ◆ shows Comparative Example 6, ○ shows Comparative Example 7, and • shows Comparative Example 8.

In FIGS. 5 and 6, plots ■ (Comparative Example 3) and ◆ (Comparative Example 6) overlap.

In addition, in FIG. 7, plots other than plots ▲ (Comparative Example 4) and ○ (Comparative Example 7) overlap.

In addition, to investigate the temperature dependences, the temperature was changed to 80° C. in Comparative Example 2 and Comparative Example 5, and the measurement was performed under the same conditions as those in Comparative Example 1.

Figure 8:
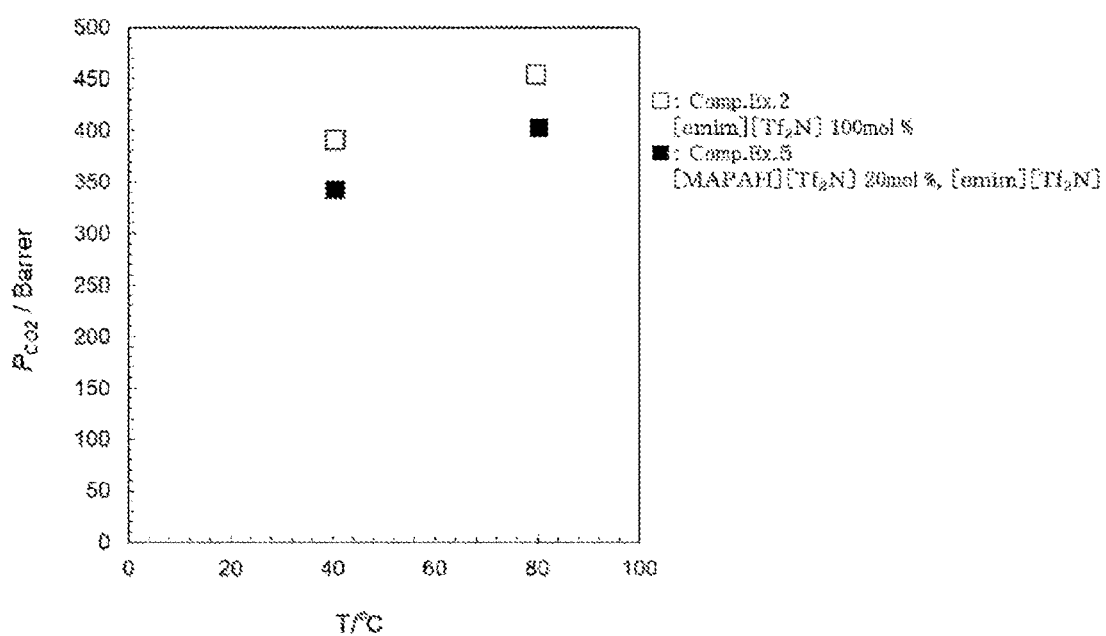
FIG. 8 is a graph showing temperature dependences of $CO_2$ permeability coefficients of the [emim][$Tf_2N$]-based $CO_2$ separation membranes (Comparative Examples 2 and 5).
Figure 9:
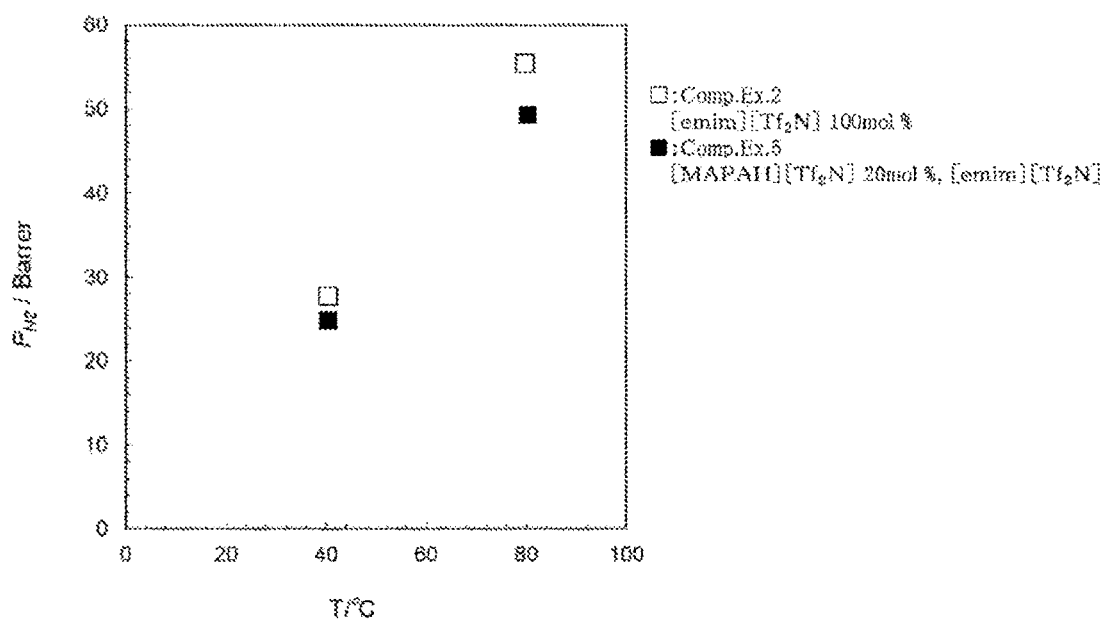
FIG. 9 is a graph showing temperature dependences of $N_2$ permeability coefficients of the [emim][$Tf_2N$]-based $CO_2$ separation membranes (Comparative Examples 2 and 5).
Figure 10:
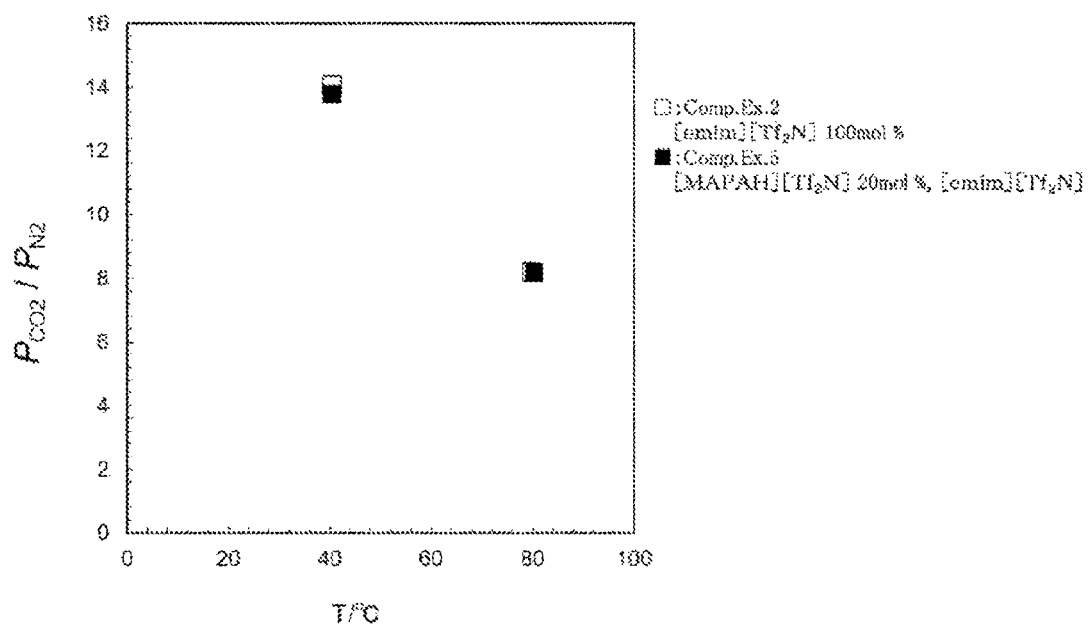
FIG. 10 is a graph showing temperature dependences of $CO_2$ selectivity ratios of the [emim][$Tf_2N$]-based $CO_2$ separation membranes (Comparative Examples 2 and 5).

The temperature dependences of the resulting $CO_2$ permeability coefficient, $N_2$ permeability coefficient, and $CO_2$ selectivity ratio are shown in FIGS. 8, 9, and 10,
where □ shows Comparative Example 2, and ■ shows Comparative Example 5.

SUMMARY

As is clear from FIGS. 5 and 7, the $CO_2$ permeability coefficient and the $CO_2$ selectivity ratio decreased in Comparative Example 3 (■), Comparative Example 5 (◇), and Comparative Example 6 (◆) compared with those in Comparative Example 2 (□) using [emim][$Tf_2N$]. It is found that mixing [emim][$Tf_2N$] with [APAH][$Tf_2N$], [MAPAH][$Tf_2N$], or [DMAPAH][$Tf_2N$] is not effective in improving the $CO_2$ permeation selectivity of the separation membrane.

In addition, as is clear from FIGS. 8 and 10, even though the temperature was increased from 40° C. to 80° C., the $CO_2$ permeation selectivity of Comparative Example 5 (■) remained lower than that of Comparative Example 2 (□).

Furthermore, as is clear from FIGS. 5 and 7, in Comparative Example 4 (▲) using [omim][$Tf_2N$] in which the alkyl chain of the imidazolium cation was lengthened in place of [emim][$Tf_2N$] of Comparative Example 3 (■), the $CO_2$ permeability coefficient and the $CO_2$ selectivity ratio further decreased compared with those in Comparative Example 3.

Moreover, in Comparative Example 4, the $N_2$ permeability coefficient increased compared with that in Comparative Example 3. On the other hand, as shown in FIGS. 5 and 7, the $CO_2$ permeability coefficient and the $CO_2$ selectivity ratio of Comparative Example 7 (○) were higher than those of Comparative Examples 2 (□) and 8 (•).

As is clear from FIGS. 2 and 3, in Comparative Example 1 using [emim][DCA], the $CO_2$ permeability coefficient and the $N_2$ permeability coefficient were lower than those in Comparative Examples 2, 3, 4, 5, and 6 shown in FIGS. 5 and 6. On the other hand, as is clear from FIG. 4, the $CO_2$ selectivity ratio of Comparative Example 1 was higher than those of Comparative Examples 2 to 6.

As described above, mixing [emim][Tf$_2$N] with [HDAH][Tf$_2$N] having a hydroxyl group and an amino group in the cation was found to improve the $CO_2$ permeation selectivity compared with using only each ionic liquid. However, the resulting $CO_2$ permeation selectivity was not yet sufficient.

Thus, in place of [emim][Tf$_2$N], using an ionic liquid having an oxoacid anion as the ionic liquid (II) was investigated. The ionic liquid having an oxoacid anion (hydrogen bond accepting ionic liquid) has even better solubility for a product after $CO_2$ absorption than [emim][Tf$_2$N] described above in a solvent of a chemical absorption liquid (see Patent Document 4 and Non-Patent Literature 1 described above).

Examples 1 to 6, and Comparative Example 9

In Examples 1 to 6 and Comparative Example 9, as the ionic liquid (II), 1-ethyl-3-methylimidazolium methylphosphonate ([emim][MeHPO$_3$]), which has methylphosphonate, one of oxoacid anions, as the anion, was used.

Example 1

[HDAH][Tf$_2$N] described above and [emim][MeHPO$_3$] described above were mixed, and a mixed liquid ([HDAH][Tf$_2$N]20 mol %) was prepared.

The resulting mixed liquid was impregnated into the hydrophilized PTFE filter in the same manner as described above, and a $CO_2$ separation membrane was prepared as Example 1.

Examples 2 to 6 and Comparative Example 9

$CO_2$ separation membranes were prepared as Examples 2 to 5 and Comparative Example 9 in the same manner as in Example 1 except that the composition of [HDAH][Tf$_2$N] in Example 1 was changed as shown in Table 2 below. In addition, a $CO_2$ separation membrane was prepared as Example 6 in the same manner as in Example 1 except that [HDAH][Tf$_2$N] in Example 1 was changed to [APAH][Tf$_2$N]. Comparative Example 8 (composition 100 mol %) described above is additionally listed in Table 2.

TABLE 2

| | Ionic liquid (I) | Composition (mol %) of ionic liquid (I) | Ionic liquid (II) |
| --- | --- | --- | --- |
| Example 1 | [HDAH][Tf$_2$N] | 20 | [emim][MeHPO$_3$] |
| Example 2 | [HDAH][Tf$_2$N] | 5 | [emim][MeHPO$_3$] |
| Example 3 | [HDAH][Tf$_2$N] | 10 | [emim][MeHPO$_3$] |
| Example 4 | [HDAH][Tf$_2$N] | 40 | [emim][MeHPO$_3$] |
| Example 5 | [HDAH][Tf$_2$N] | 80 | [emim][MeHPO$_3$] |
| Example 6 | [APAH][Tf$_2$N] | 20 | [emim][MeHPO$_3$] |
| Comparative Example 9 | — | 0 | [emim][MeHPO$_3$] |
| Comparative Example 8 | [HDAH][Tf$_2$N] | 100 | — |

The gas permeability coefficients of Examples 1 to 6 and Comparative Example 9 were measured using four $CO_2/N_2$ mixed gases with different $CO_2$ composition described above at a temperature of 40° C., a feed side gas flow rate of 100 mL/min, and a permeating side gas flow rate of 20 mL/min, and the composition dependences and the $CO_2$ partial pressure dependences were investigated.

Figure 11:
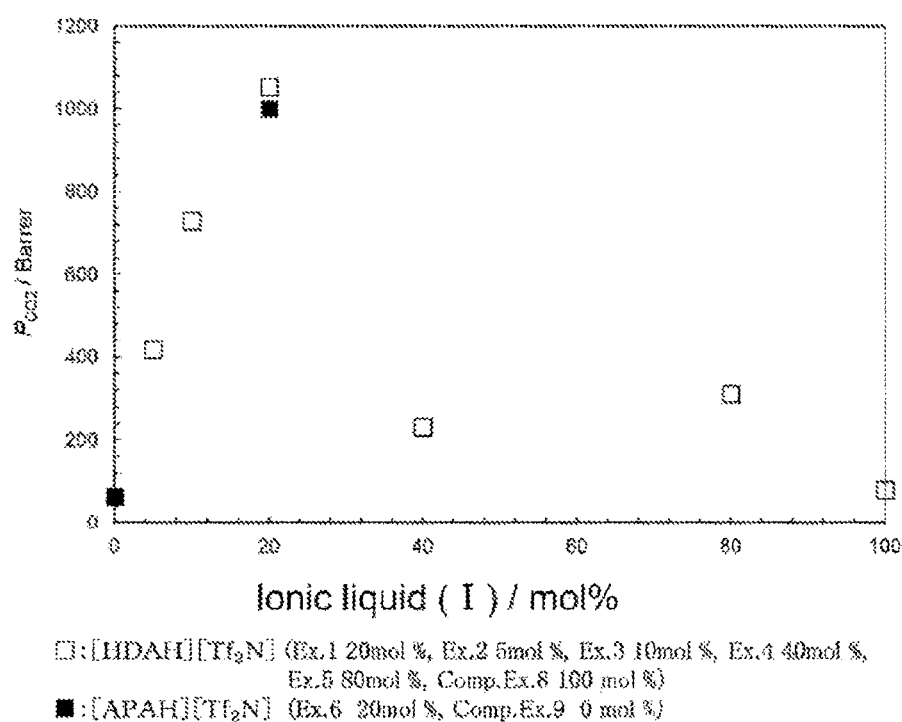
FIG. 11 is a graph showing composition dependences of $CO_2$ permeability coefficients of [emim][$MeHPO_3$]-based $CO_2$ separation membranes (Examples 1 to 6 and Comparative Examples 8 and 9).
Figure 12:
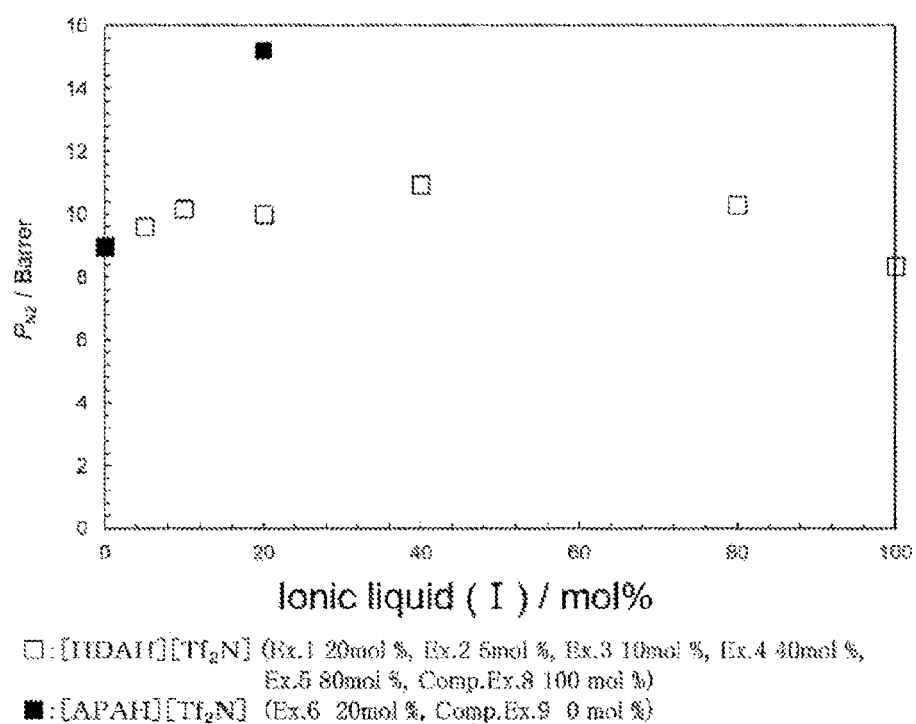
FIG. 12 is a graph showing composition dependences of $N_2$ permeability coefficients of the [emim][$MeHPO_3$]-based $CO_2$ separation membranes (Examples 1 to 6 and Comparative Examples 8 and 9).
Figure 13:
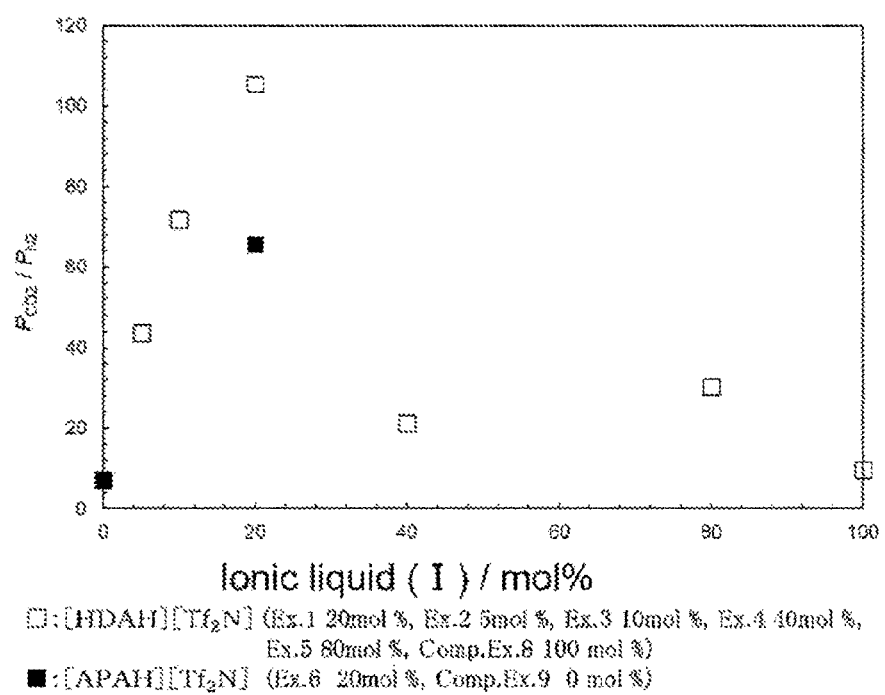
FIG. 13 is a graph showing composition dependences of $CO_2$ selectivity ratios of the [emim][$MeHPO_3$]-based $CO_2$ separation membranes (Examples 1 to 6 and Comparative Examples 8 and 9).

The composition dependences of the resulting $CO_2$ permeability coefficient, $N_2$ permeability coefficient, and $CO_2$ selectivity ratio at a $CO_2$ partial pressure of 0.04 kPa ($CO_2$ composition 0.04 mol %) are shown in FIGS. 11, 12, and 13, where Comparative Example 8 (composition 100 mol %) described above is additionally shown, and □ shows Examples 1 to 5 and Comparative Examples 8 and 9, and ■ shows Example 6 and Comparative Example 9.

Figure 14:
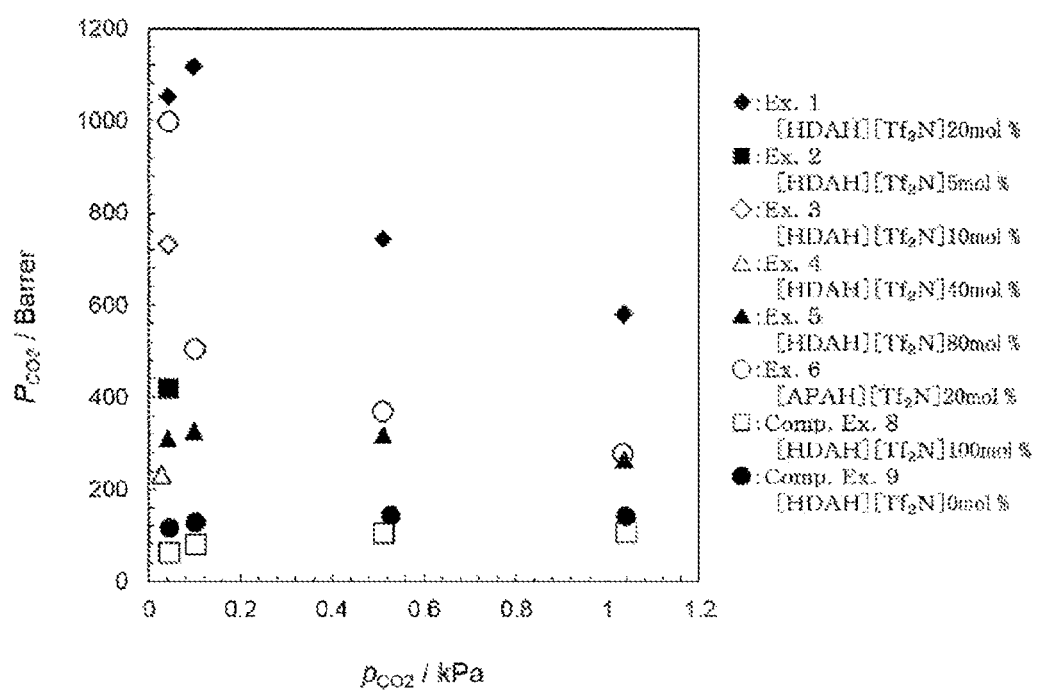
FIG. 14 is a graph showing $CO_2$ partial pressure dependences of $CO_2$ permeability coefficients of the [emim][$MeHPO_3$]-based $CO_2$ separation membranes (Examples 1 to 6 and Comparative Examples 8 and 9).
Figure 15:
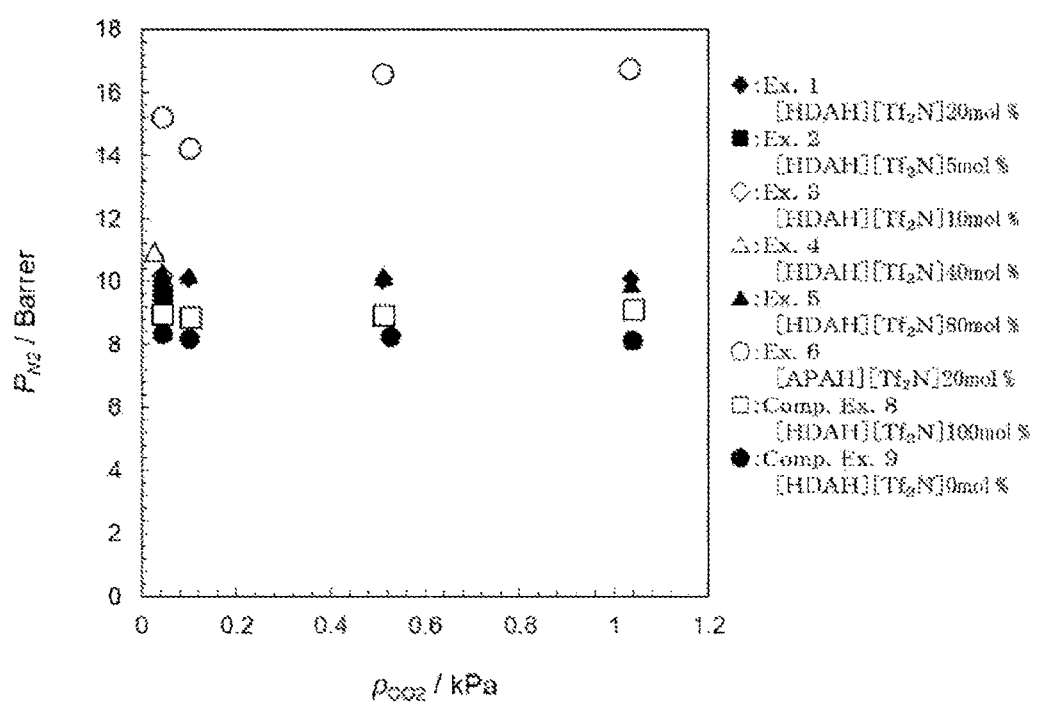
FIG. 15 is a graph showing $CO_2$ partial pressure dependences of $N_2$ permeability coefficients of the [emim][$MeHPO_3$]-based $CO_2$ separation membranes (Examples 1 to 6 and Comparative Examples 8 and 9).
Figure 16:
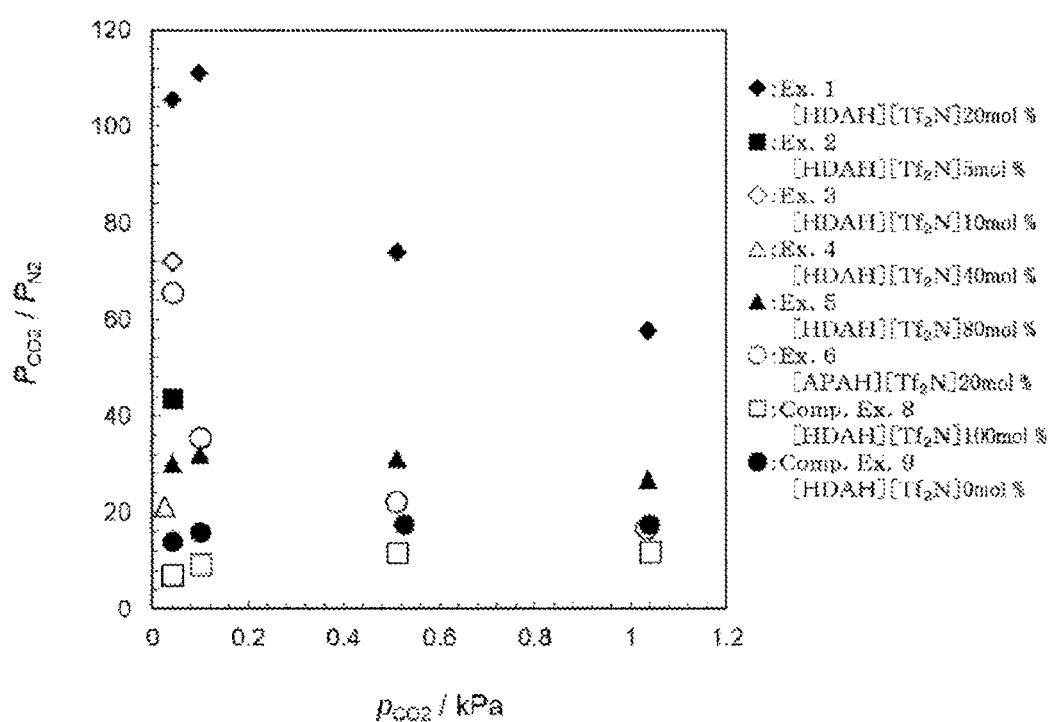
FIG. 16 is a graph showing $CO_2$ partial pressure dependences of $CO_2$ selectivity ratios of the [emim][$MeHPO_3$]- based CO₂ separation membranes (Examples 1 to 6 and Comparative Examples 8 and 9).

In addition, the $CO_2$ partial pressure dependences of the $CO_2$ permeability coefficient, $N_2$ permeability coefficient, and $CO_2$ selectivity ratio are shown in FIGS. 14, 15, and 16, where Comparative Example 8 (composition 100 mol %) described above is also additionally shown, and ♦ shows Example 1, ■ shows Example 2, ◇ shows Example 3, Δ shows Example 4, ▲ shows Example 5, ○ shows Example 6, □ shows Comparative Example 8, and • shows Comparative Example 9.

In FIG. 15, plots ♦ (Example 1), ◇ (Example 3), and ▲ (Example 5) overlap.

SUMMARY

As is clear from FIGS. 11 and 13, the $CO_2$ separation membranes prepared by mixing [HDAH][Tf$_2$N] and [emim][MeHPO$_3$](Examples 1 to 5)(□) exhibited improved $CO_2$ permeability coefficients and maintained the $N_2$ permeability coefficients almost constantly, and this greatly improved the $CO_2$ selectivity ratios compared with the $CO_2$ separation membrane prepared using only [HDAH][Tf$_2$N](Comparative Example 8)(□) and the $CO_2$ separation membrane prepared using only [emim][MeHPO$_3$](Comparative Example 9)(■).

In addition, as is clear from FIGS. 14 and 16, the $CO_2$ separation membrane with a mixing ratio of 20:80 (Example 1) (♦) and the $CO_2$ separation membrane with a mixing ratio of 80:20 (Example 5) (▲) exhibited improved $CO_2$ permeability coefficients and improved $CO_2$ selectivity ratios along with the decrease in $CO_2$ partial pressure, and furthermore exhibited higher $CO_2$ permeability coefficients and higher $CO_2$ selectivity ratios than Comparative Examples 8 (□) and 9 (•) under $CO_2$ partial pressure conditions up to 1 kPa. In Comparative Examples 8 and 9, no $CO_2$ partial pressure dependence as in Examples 2 and 5 was observed, and the $CO_2$ permeability coefficients, the $N_2$ permeability coefficients, and the $CO_2$ selectivity ratios remained almost constant.

In addition, as can be seen from FIGS. 11 and 13 as well as from FIGS. 5 and 7 described above, the $CO_2$ separation membrane prepared by mixing [APAH][Tf$_2$N] and [emim][MeHPO$_3$](Example 6) (■) exhibited higher $CO_2$ permeability coefficients and higher $CO_2$ selectivity ratios than the $CO_2$ separation membrane prepared using only [emim][Tf$_2$N](Comparative Example 2) (◆), the $CO_2$ separation membrane prepared by mixing [APAH][Tf$_2$N] and [emim][Tf$_2$N](Comparative Example 3) (■), and the $CO_2$ separation membrane prepared using only [emim][MeHPO$_3$] (Comparative Example 9) (■).

Such improved effects were not observed in the $CO_2$ separation membrane prepared by mixing [emim][Tf$_2$N], an ionic liquid with a weak hydrogen bond acceptability, and [APAH][Tf$_2$N](Comparative Example 3) (■).

As described above, the results revealed that the $CO_2$ separation membrane prepared using the ionic liquid composition prepared by mixing the aminium having an amino group (regardless of having a hydroxyl group) and [emim][MeHPO$_3$] prepared using methylphosphonate, one of oxoacid anions, for the anion improves $CO_2$ permeation selectivity compared with the $CO_2$ separation membrane prepared using only each ionic liquid.

Thus, to verify whether similar excellent effects are obtained with an ionic liquid having another oxoacid anion, in place of [emim][MeHPO$_3$], using 1-ethyl-3-methylimidazolium acetate ([emim][AcO]) or 1-ethyl-3-methylimidazolium 3-(2-methoxyethoxy)propionate ([emim][102OPrO]) as the ionic liquid (II) was investigated.

Examples 7 to 11 and Comparative Example 10

In Examples 7 to 11 and Comparative Example 10, acetate, one of oxoacid anions, was used as the ionic liquid (II).

Example 7

[HDAH][Tf$_2$N] described above was used as the ionic liquid (I), and [emim][AcO] as the ionic liquid (II) was mixed therewith, and a mixed liquid ([HDAH][Tf$_2$N]5 mol %) was prepared.

The resulting mixed liquid was impregnated into the hydrophilized PTFE filter in the same manner as described above, and a $CO_2$ separation membrane was prepared as Example 7.

Examples 8 to 11 and Comparative Example 10

$CO_2$ separation membranes were prepared as Examples 8 to 11 and Comparative Example 10 in the same manner as in Example 7 except that the composition (mol %) of [HDAH][Tf$_2$N] in Example 7 was changed as shown in Table 3 below. Comparative Example 8 (100 mol %) described above is additionally listed in Table 2.

TABLE 3

| | Ionic liquid (I) | Composition (mol %) of ionic liquid (I) | Ionic liquid (II) |
| --- | --- | --- | --- |
| Example 7 | [HDAH][Tf$_2$N] | 5 | [emim][AcO] |
| Example 8 | [HDAH][Tf$_2$N] | 10 | [emim][AcO] |
| Example 9 | [HDAH][Tf$_2$N] | 20 | [emim][AcO] |
| Example 10 | [HDAH][Tf$_2$N] | 40 | [emim][AcO] |
| Example 11 | [HDAH][Tf$_2$N] | 80 | [emim][AcO] |

TABLE 3-continued

| | Ionic liquid (I) | Composition (mol %) of ionic liquid (I) | Ionic liquid (II) |
| --- | --- | --- | --- |
| Comparative Example 10 | — | 0 | [emim][AcO] |
| Comparative Example 8 | [HDAH][Tf$_2$N] | 100 | — |

The gas permeability coefficients of Examples 7 to 11 and Comparative Example 10 were measured at a temperature of 40° C., a feed side gas flow rate of 100 mL/min, and a permeating side gas flow rate of 20 mL/min, and the composition dependences of the $CO_2$ permeability coefficient, $N_2$ permeability coefficient, and $CO_2$ selectivity ratio were examined.

The composition dependences of the resulting $CO_2$ permeability coefficient and $N_2$ permeability coefficient at a $CO_2$ partial pressure of 0.04 kPa ($CO_2$ composition 0.04 mol %) are shown in FIG. 17, where Comparative Example 8 (composition 100 mol %) described above is additionally shown, and □ shows the $CO_2$ permeability coefficients of Examples 7 to 11 and Comparative Examples 8 and 10, ■ shows $N_2$ permeability coefficients of Examples 7 to 11 and Comparative Examples 8 and 10.

The composition dependence of the $CO_2$ selectivity ratio is shown in FIG. 18 by ◇, where Comparative Example 8 (composition 100 mol %) (◆) is also additionally shown.

Furthermore, for Example 8 and Comparative Example 10, the gas permeability coefficients were measured using four $CO_2/N_2$ mixed gases with different $CO_2$ composition described above at 40° C., and the $CO_2$ partial pressure dependences of the $CO_2$ permeability coefficient, $N_2$ permeability coefficient, and $CO_2$ selectivity ratio were investigated.

Comparative Example 10 was measured at a feed side gas flow rate of 100 mL/min and a permeating side gas flow rate of 20 mL/min as described above, and Example 8 was measured at a feed side gas flow rate of 400 mL/min and a permeating side gas flow rate of 200 mL/min.

The $CO_2$ partial pressure dependences of the resulting $CO_2$ permeability coefficient, $N_2$ permeability coefficient, and $CO_2$ selectivity ratio are shown in FIGS. 19, 20, and 21, where ■ shows Example 8, and ◆ shows Comparative Example 10.

As shown in FIG. 19, increasing the gas flow rate improved the $CO_2$ permeability coefficient in Example 8 compared with FIG. 17. This is because the increase in the gas flow rate reduced the $CO_2$ partial pressure on the permeating side, and this increased the $CO_2$ partial pressure difference between the feed side and the permeating side. However, in the separation membrane of Comparative Example 10 with a low $CO_2$ permeability coefficient, even increasing the permeation gas flow rate does not change the $CO_2$ permeability coefficient.

Examples 12 and 13

In Examples 12 and 13, the differences of the substrates used were investigated.

Example 12

A $CO_2$ separation membrane was prepared as Example 12 in the same manner as in Example 8 except that the mixed liquid of [HDAH][Tf$_2$N] and [emim][AcO]([HDAH][Tf$_2$N] 10 mol %) used in Example 8 was impregnated into an alumina-coated filter.

Example 13

A CO$_2$ separation membrane was prepared as Example 13 in the same manner as in Example 12 except that the mixed liquid was impregnated into a titania-coated filter.

The gas permeability coefficients of Examples 12 and 13 were measured using four CO$_2$/N$_2$ mixed gases with different CO$_2$ composition described above at a feed side gas flow rate of 400 mL/min and a permeating side gas flow rate of 200 mL/min, and the CO$_2$ partial pressure dependences were investigated.

The CO$_2$ partial pressure dependences of the resulting CO$_2$ permeability coefficient, N$_2$ permeability coefficient, and CO$_2$ selectivity ratio are shown in FIGS. 19, 20, and 21 described above, where Example 8 and Comparative Example 10 (100 mol %) described above are additionally shown, and ■ shows Example 8, ◇ shows Example 12, ○ shows Example 13, and ◆ shows Comparative Example 10.

Example 14

In place of [HDAH][Tf$_2$N] used in Example 8, [APAH][Tf$_2$N] was used, and [emim][AcO] as the ionic liquid (II) was mixed to this, and a mixed liquid ([APAH][Tf$_2$N]10 mol %) was prepared.

The resulting mixed liquid was impregnated into the hydrophilized PTFE filter in the same manner as described above, and a CO$_2$ separation membrane was prepared as Example 14.

The gas permeability coefficients of Example 14 were measured at a temperature of 40° C., a feed side gas flow rate of 400 mL/min, and a permeating side gas flow rate of 40 mL/min, and the composition dependences were investigated.

The composition dependences of the resulting CO$_2$ permeability coefficient, N$_2$ permeability coefficient, and CO$_2$ selectivity ratio at a CO$_2$ partial pressure of 0.04 kPa (CO$_2$ composition 0.04 mol %) are shown in FIGS. 22, 23, and 24 by A, where Example 8 ([HDAH][Tf$_2$N] composition 10 mol %) and Comparative Example 8 ([HDAH][Tf$_2$N] composition 100 mol %) described above are additionally shown by □.

Example 15 and Comparative Example 11

In Example 15 and Comparative Example 11, as shown in Table 4 below, 3-(2-methoxyethoxy)propionate, one of oxoacid anions, was used as the ionic liquid (II). In Table 4, Comparative Example 8 described above is additionally listed.

Example 15

A CO$_2$ separation membrane was prepared as Example 15 in the same manner as in Example 14 except that a mixed liquid ([HDAH][Tf$_2$N]10 mol %) prepared by mixing [HDAH][Tf$_2$N] and [emim][1O2OPrO] obtained in Synthesis Example 8 described above was used.

Comparative Example 11

A CO$_2$ separation membrane was prepared as Comparative Example 11 in the same manner as in Example 15 except that only [emim][1O2OPrO] in Example 15 was used.

TABLE 4

| | Ionic liquid (I) | Composition (mol %) of ionic liquid (I) | Ionic liquid (II) |
|---|---|---|---|
| Example 15 | [HDAH][Tf$_2$N] | 10 | [emim][1O2OPro] |
| Comparative Example 8 | [HDAH][Tf$_2$N] | 100 | — |
| Comparative Example 11 | — | 0 | [emim][1O2OPro] |

The gas permeability coefficients of Example 15 and Comparative Example 11 were measured at 40° C., and the composition dependences were investigated.

Example 15 was measured at a feed side gas flow rate of 400 mL/min and a permeating side gas flow rate of 200 mL/min, and Comparative Example 11 was measured at a feed side gas flow rate of 100 mL/min and a permeating side gas flow rate of 20 mL/min.

The composition dependences of the resulting CO$_2$ permeability coefficient and N$_2$ permeability coefficient at a CO$_2$ partial pressure of 0.04 kPa (CO$_2$ composition 0.04 mol %) are shown in FIG. 17, where ◇ shows the CO$_2$ permeability coefficients of Example 15 and Comparative Examples 8 and 11, and ◆ shows N$_2$ permeability coefficients of Example 15 and Comparative Examples 8 and 11.

Plots of the N$_2$ permeability coefficient of Example 15 (◆) and those of Example 8 (■) overlap.

In addition, the composition dependence of the resulting CO$_2$ selectivity ratio is shown in FIG. 18 described above by ◆.

SUMMARY

FIGS. 17 and 18 revealed that the CO$_2$ separation membranes prepared using the ionic liquid prepared by mixing [HDAH][Tf$_2$N] and [emim][AcO](Examples 7 to 10) exhibit higher CO$_2$ permeability coefficients and higher CO$_2$ selectivity ratios compared with the CO$_2$ separation membranes prepared using each pure ionic liquid (Comparative Examples 8 and 10).

In addition, the CO$_2$ separation membrane prepared using the ionic liquid prepared by mixing [HDAH][Tf$_2$N] and [emim][AcO](Example 11) also exhibited even better CO$_2$ permeation selectivity than the CO$_2$ separation membrane prepared using only [HDAH][Tf$_2$N](Comparative Example 8).

As can be seen from FIGS. 19 and 21, this significant improved effect was also observed in cases where the membrane substrate was changed from the hydrophilized PTFE filter (Example 8) to the alumina-coated filter (Example 12) and the titania-coated filter (Example 13).

In addition, as is clear from FIGS. 22 and 24, the CO$_2$ separation membrane prepared by changing [HDAH][Tf$_2$N] of Example 8 (□) to [APAH][Tf$_2$N](Example 14) (△) also exhibited a higher CO$_2$ permeability coefficient and a higher $CO_2$ selectivity ratio than the $CO_2$ separation membrane prepared using only [emim][AcO](Comparative Example 10) (■).

Furthermore, as described in FIGS. 17 and 18, when [emim][AcO] of Example 8 (■, ◇) was changed to [emim][1O2OPrO](Example 15)(♦, ◆), Example 15 exhibited lowered $CO_2$ permeation selectivity compared with Example 8 but still exhibited a higher $CO_2$ permeability coefficient and a higher $CO_2$ selectivity ratio than the $CO_2$ separation membrane prepared using only [HDAH][Tf$_2$N](Comparative Example 8) (◇, ◆), the $CO_2$ separation membrane prepared using only [emim][AcO](Comparative Example 10) (□, ◇), and the $CO_2$ separation membrane prepared using only [emim][1O2OPrO](Comparative Example 11) (♦, ◆).

Furthermore, compared with Example 1 (Q in FIGS. 11 and 13), Example 8 (Q in FIG. 17, ◇ in FIG. 18) and Example 15 (◇ in FIG. 17, ♦ in FIG. 18) exhibited a high $CO_2$ permeability coefficient and a high $CO_2$ selectivity ratio. This revealed that the composition prepared using the ionic liquid having carboxylates (acetate and 3-(2-methoxyethoxy)propionate) as the anions can provide a $CO_2$ separation membrane having even better $CO_2$ permeation selectivity than the composition prepared using the ionic liquid having a phosphonate (methylphosphonate) as the anion.

Examples 16 to 20 and Comparative Example 12

Effects of the ionic liquid (I) other than [HDAH][Tf$_2$N] and [APAH][Tf$_2$N] were investigated using 2-aminoethylaminium bis(trifluoromethylsulfonyl)amide ([EDAH][Tf$_2$N]) obtained in Synthesis Example 5 above, 2-(2-(aminoethyl)amino)ethylaminium bis(trifluoromethylsulfonyl)amide ([DETAH][Tf$_2$N]) obtained in Synthesis Example 6 above, or 2-(2-(2-(aminoethyl)aminoethyl)amino)ethylaminium bis(trifluoromethylsulfonyl)amide ([TETAH][Tf$_2$N]) obtained in Synthesis Example 7 above.

Example 16

A mixed liquid was prepared by mixing [EDAH][Tf$_2$N] and [emim][AcO] as shown in Table 5 below. In Table 5, Example 14 and Comparative Example 10 described above are additionally listed.

The resulting mixed liquid was impregnated into the hydrophilized PTFE filter in the same manner as described above, and a $CO_2$ separation membrane was prepared as Example 16.

Examples 17 to 20 and Comparative Example 12

$CO_2$ separation membranes were prepared as Examples 17 to 20 and Comparative Example 12 in the same manner as in Example 16 except that [EDAH][Tf$_2$N] in Example 16 was changed as shown in Table 5 below.

TABLE 5

|  | Ionic liquid (I) | Composition (mol %) of ionic liquid (I) | Ionic liquid (II) |
| --- | --- | --- | --- |
| Example 14 | [APAH][Tf$_2$N] | 10 | [emim][AcO] |
| Example 16 | [EDAH][Tf$_2$N] | 10 | [emim][AcO] |
| Example 17 | [DETAH][Tf$_2$N] | 5 | [emim][AcO] |
| Example 18 | [DETAH][Tf$_2$N] | 10 | [emim][AcO] |
| Example 19 | [DETAH][Tf$_2$N] | 20 | [emim][AcO] |
| Example 20 | [TETAH][Tf$_2$N] | 10 | [emim][AcO] |
| Comparative Example 10 | — | 0 | [emim][AcO] |
| Comparative Example 12 | [TETAH][Tf$_2$N] | 100 | |

The gas permeability coefficients of Examples 16 to 20 and Comparative Example 12 were measured at a temperature of 40° C., a feed side gas flow rate of 400 mL/min, and a permeating side gas flow rate of 200 mL/min, and the composition dependences were investigated.

The composition dependences of the resulting $CO_2$ permeability coefficient, $N_2$ permeability coefficient, and $CO_2$ selectivity ratio at a $CO_2$ partial pressure of 0.04 kPa ($CO_2$ composition 0.04 mol %) are shown in FIGS. 22, 23, and 24 described above.

These figures also include Example 8 (composition 10 mol %) and Comparative Example 8 (composition 100 mol %) using [HDAH][Tf$_2$N] described above, and Example 14 (composition 10 mol %) and Comparative Example 10 (composition 0 mol %) using ([APAH][Tf$_2$N] described above.

In the figures, □ shows Example 8 and Comparative Example 8, Δ shows Example 14, ■ shows Example 16 and Comparative Example 10, ◇ shows Examples 17 to 19, and ♦ shows Example 20 and Comparative Example 12.

Summary

As can be seen from FIGS. 22 and 24, the $CO_2$ separation membrane composed of the ionic liquid composition prepared by mixing [EDAH][Tf$_2$N], [DETAH][Tf$_2$N], or [TETAH][Tf$_2$N] with [emim][AcO](Examples 16 to 20) exhibited a higher $CO_2$ permeability coefficient and a higher $CO_2$ selectivity ratio than the $CO_2$ separation membrane composed of the ionic liquid composition of only [emim][AcO] (Comparative Example 10) or the $CO_2$ separation membrane composed of the ionic liquid composition of only [TETAH][Tf$_2$N](Comparative Example 12). Comparing these also with Examples 8 and 14 revealed that the $CO_2$ permeability coefficient was highest with [HDAH][Tf$_2$N](Example 8) and decreased in the order of [DETAH][Tf$_2$N](Example 18), [TETAH][Tf$_2$N](Example 20), [APAH][Tf$_2$N](Example 14), and [EDAH][Tf$_2$N](Example 16).

As described above, changing the molecular structure of the aminium of the ionic liquid (I) in an embodiment of the present invention was found to improve the $CO_2$ permeation selectivity of the $CO_2$ separation membrane.

Examples 21 and 22 and Comparative Examples 13 and 14

Effects of a cation other than [emim] above in the ionic liquid (II) were investigated using N,N-diethyl-N-methyl-N-heptylammonium acetate ([N$_{1227}$][AcO]) obtained in Synthesis Example 9 above or N,N-diethyl-N-methyl-N-(6-hydroxyhexyl)ammonium acetate ([N$_{1226OH}$][AcO]) obtained in Synthesis Example 10 above.

Examples 21 and 22

Mixed liquids were prepared by mixing [HDAH][Tf$_2$N] and [N$_{1227}$][AcO] or [N$_{1226OH}$][AcO] as shown in Table 6 below. The resulting mixed liquids were each used to impregnate the hydrophilized PTFE filter in the same manner as described above, and $CO_2$ separation membranes were each prepared as Examples 21 and 22.

Comparative Examples 13 and 14

$CO_2$ separation membranes were prepared as Comparative Examples 13 and 14 in the same manner as in Examples 21 and 22 except that only [$N_{1227}$][AcO] or [$N_{1226OH}$][AcO] was used in Example 21 or 22. Comparative Example 8 (composition 100 mol %) described above is additionally listed in Table 6.

TABLE 6

| | Ionic liquid (I) | Composition (mol %) of ionic liquid (I) | Ionic liquid (II) |
|---|---|---|---|
| Example 21 | [HDAH][Tf$_2$N] | 10 | [N$_{1227}$][AcO] |
| Comparative Example 13 | — | 0 | [N$_{1227}$][AcO] |
| Example 22 | [HDAH][Tf$_2$N] | 10 | [N$_{1226}$OH][AcO] |
| Comparative Example 14 | — | 0 | [N$_{1226}$OH][AcO] |
| Comparative Example 8 | [HDAH][Tf$_2$N] | 100 | — |

The gas permeability coefficients of Examples 21 and 22 and Comparative Examples 13 and 14 were measured at a temperature of 40° C., a feed side gas flow rate of 400 mL/min, and a permeating side gas flow rate of 20 to 40 mL/min, and the composition dependences were investigated.

The composition dependences of the resulting $CO_2$ permeability coefficient, $N_2$ permeability coefficient, and $CO_2$ selectivity ratio at a $CO_2$ partial pressure of 0.04 kPa ($CO_2$ composition 0.04 mol %) are shown in FIGS. 25, 26, and 27, where Comparative Example 8 ([HDAH][Tf$_2$N] composition 100 mol %) described above is additionally shown, and □ shows Example 21, ■ shows Example 22, ◇ shows Comparative Example 13, ◆ shows Comparative Example 14, and Δ shows Comparative Example 8.

SUMMARY

As can be seen from FIGS. 25 and 27, the $CO_2$ separation membrane composed of the ionic liquid composition prepared by mixing [$N_{1227}$][AcO] or [$N_{1226OH}$][AcO] to [HDAH][Tf$_2$N](Examples 21 or 22) exhibited a higher $CO_2$ permeability coefficient and a higher $CO_2$ selectivity ratio than the $CO_2$ separation membrane composed of the ionic liquid composition of only [$N_{1227}$][AcO] or [$N_{1226OH}$][AcO](Comparative Example 13 or Comparative Example 14) or the $CO_2$ separation membrane composed of the ionic liquid composition of only [HDAH][Tf$_2$N](Comparative Example 8).

As described above, changing the molecular structure of the cation to the ammonium in the ionic liquid (II) having an oxoacid anion was also found to improve the $CO_2$ permeation selectivity of the $CO_2$ separation membrane.

Overall Summary

The $CO_2$ separation membranes prepared using the composition prepared by mixing two ionic liquids (I) and (II) were revealed to exhibit a higher $CO_2$ permeability coefficient and a higher $CO_2$ selectivity ratio compared with the $CO_2$ separation membranes prepared using each pure ionic liquid. The ionic liquid (I) is an ionic liquid having as the cation an aminium having a primary amino group and/or a secondary amino group. The ionic liquid (II) is a hydrogen bond-accepting ionic liquid with excellent $CO_2$ solubility and excellent solubility for a product after $CO_2$ absorption, the ionic liquid having a cation having no primary or secondary amino group and having an oxoacid anion, such as a carboxylate, a phosphinate, or a phosphonate. When the composition of the ionic liquid (I) is in the range preferably of 5 mol % to 80 mol % and particularly preferably of 5 mol % to 40 mol %, higher improved effect on the $CO_2$ permeation selectivity is observed. On the other hand, using the ionic liquid, such as [emim][Tf$_2$N], having no oxoacid anion fails to obtain the excellent effect in the present invention of improving the permeability and permeation selectivity of carbon dioxide, which is clear from examples and comparative examples.

That is, for the ionic liquid composition according to an embodiment of the present invention, the following can be said: using the aminium-based ionic liquid (I) having an amino group and the ionic liquid (II) with excellent hydrogen bond acceptability, the ionic liquid (II) having an oxoacid anion, such as a carboxylate, a phosphate, or a phosphonate, was able to not only increase the solubility of carbon dioxide but also improve the diffusion rate of the carrier chemically reacted with carbon dioxide, and consequently was able to significantly improve the permeability and permeation selectivity of carbon dioxide of the carbon dioxide separation membrane.

INDUSTRIAL APPLICABILITY

An embodiment of the present invention can efficiently separate and recover carbon dioxide from high partial pressure to a low partial pressure of 1 kPa or lower and thus, needless to say, can be used in a process for separating and recovering carbon dioxide having high partial pressure discharged from biogas production equipment, biomass power generation equipment, an incinerator, a chemical plant, a steel plant, a power plant, or the like and can also be used to separate and recover carbon dioxide having a low partial pressure of 1 kPa or lower at high speed and high energy efficiency, the carbon dioxide being contained, for example, in the atmosphere or in air in an environment, such as a high-rise building or closed working space, where normal ventilation is difficult. This enables unused carbon dioxide to be used, for example, to promote the growth of plants and algae. In addition, carbon dioxide in a space can be removed without ventilation, and this eliminates the need for discharging the thermal energy of the space to the outside of the space and thus can reduce the energy required for air conditioning.

REFERENCE SIGNS LIST

1: $CO_2/N_2$ standard gas cylinder
2: $N_2$ gas cylinder
3: Ar gas cylinder
4 to 6: Mass flow controller
7: $CO_2$ separation membrane
8: Separation membrane holder
9: Oven
10, 11: Thermo-hygrometer
12, 14: Trap
13: Chiller 15, 16: Back pressure valve
17, 20: Soap film flow meter
18: Gas chromatograph (TCD-GC)
19: $CO_2$ densitometer

The invention claimed is:

1. A method of separating carbon dioxide by using an ionic liquid composition, comprising:
preparing a membrane having a porous layer; and
retaining the ionic liquid composition in voids in the porous layer;
wherein the ionic liquid composition contains
an ionic liquid (I) and
an ionic liquid (II),
wherein a cation in the ionic liquid (I) is an aminium having:
one or more primary or secondary amino groups; and
an ethylenediamine or propylenediamine backbone,
wherein
an anion in the ionic liquid (I) is bis(trifluoromethylsulfonyl)amide, and
a cation in the ionic liquid (II) has no primary or secondary amino group, and
an anion in the ionic liquid (II) is an oxoacid anion, wherein the oxoacid anion is selected from the group consisting of carboxylates, phosphates, phosphonates, and combinations thereof.

2. The method according to claim 1, wherein
the aminium is selected from the group consisting of 2-aminoethylaminium, 2-(N-hydroxyethylamino)ethylaminium,3-aminopropylaminium, 3-(N-methylamino)propylaminium, 2-(2-(aminoethyl)amino)ethylaminium, 2-(2-(2-(aminoethyl)aminoethyl)amino) ethylaminium and combinations thereof.

3. The method according to claim 1, wherein the oxoacid anion is selected from the group consisting of acetate, 2-(1-methoxyethoxy)propionate, methylphosphonate and combinations thereof.

4. The method according to claim 1, wherein the cation of the ionic liquid (II) is selected from the group consisting of 1-ethyl-3-methylimidazolium, N,N-diethyl-N-methyl-N-heptylammonium, N,N-diethyl-N-methyl-N-(6-hydroxyhexyl)ammonium and combinations thereof.

5. The method according to claim 1, wherein the carbon dioxide have a partial pressure of 1 kPa or lower.

6. A carbon dioxide separation membrane, comprising:
a porous layer retaining an ionic liquid composition in voids in the porous layer wherein the ionic liquid composition containing
an ionic liquid (I); and
an ionic liquid (II),
wherein a cation in the ionic liquid (I) is an aminium having
one or more primary or secondary amino groups; and
an ethylenediamine or propylenediamine backbone,
wherein
an anion in the ionic liquid (I) is bis(trifluoromethylsulfonyl)amide, and
a cation in the ionic liquid (II) has no primary or secondary amino group, and
an anion in the ionic liquid (II) is an oxoacid anion, wherein the oxoacid anion is selected from the group consisting of carboxylates, phosphates, phosphonates and combinations thereof.

7. The carbon dioxide separation membrane according to claim 6, wherein the aminium is selected from the group consisting of 2-aminoethylaminium, 2-(N-hydroxyethylamino)ethylaminium, 3-aminopropylaminium, 3-(N-methylamino)propylaminium, 2-(2-(aminoethyl)amino)ethylaminium, 2-(2-(2-(aminoethyl)aminoethyl)amino) ethylaminium and combinations thereof.

8. The carbon dioxide separation membrane according to claim 6, wherein
the oxoacid anion is selected from the group consisting of acetate, 2-(1-methoxyethoxy)propionate, methylphosphonate and combinations thereof.

9. The carbon dioxide separation membrane according to claim 6, wherein
the cation of the ionic liquid (II) is selected from the group consisting of 1-ethyl-3-methylimidazolium, N,N-diethyl-N-methyl-N-heptylammonium, N,N-diethyl-N-methyl-N-(6-hydroxyhexyl)ammonium and combinations thereof.

10. The carbon dioxide separation membrane according to claim 6, wherein the carbon dioxide separation membrane comprises:
an ionic liquid affinitive porous layer retaining the ionic liquid composition for a carbon dioxide separation membrane in voids; and
an ionic liquid non-affinitive porous layer.

11. The carbon dioxide separation membrane according to claim 10, wherein the ionic liquid affinitive porous layer comprises an inorganic material.

12. The carbon dioxide separation membrane according to claim 11, wherein the inorganic material comprises metal oxide particles with an average particle size from 0.001 to m on a number basis.

13. The carbon dioxide separation membrane according to claim 10, wherein an average thickness of the ionic liquid affinitive porous layer is from 0.01 to 10 m.

14. A carbon dioxide concentration apparatus comprising the carbon dioxide separation membrane described in claim 6.

* * * * *